United States Patent
Anaokar et al.

(10) Patent No.: US 7,087,397 B2
(45) Date of Patent: Aug. 8, 2006

(54) METHOD FOR DETERMINING HDL CONCENTRATION FROM WHOLE BLOOD OR PLASMA

(75) Inventors: Sunil G. Anaokar, Indianapolis, IN (US); Gena Lynn Antonopoulos, Indianapolis, IN (US); Alexandra N. Muchnik, Indianapolis, IN (US)

(73) Assignee: Polymer Technology Systems, Inc,, Indianapolis, IN (US)

( * ) Notice: Subject to any disclaimer, the term of this patent is extended or adjusted under 35 U.S.C. 154(b) by 438 days.

(21) Appl. No.: 10/329,044

(22) Filed: Dec. 23, 2002

(65) Prior Publication Data

US 2003/0175153 A1    Sep. 18, 2003

Related U.S. Application Data

(60) Provisional application No. 60/342,790, filed on Dec. 21, 2001.

(51) Int. Cl.
*C12Q 1/60* (2006.01)

(52) U.S. Cl. .......................................... 435/11; 422/60

(58) Field of Classification Search ................ 435/11; 422/56, 57, 60; 436/71, 170, 169, 177
See application file for complete search history.

(56) References Cited

U.S. PATENT DOCUMENTS

| | | | |
|---|---|---|---|
| 4,144,306 A * | 3/1979 | Figueras ........................ 422/56 |
| 5,135,716 A * | 8/1992 | Thakore ........................ 422/56 |
| 5,213,965 A | 5/1993 | Jones |
| 5,286,626 A | 2/1994 | Law et al. |
| 5,316,916 A | 5/1994 | Jones |
| 5,407,836 A | 4/1995 | Ziegenhorn et al. |
| 5,411,870 A | 5/1995 | Law et al. |
| 5,426,030 A * | 6/1995 | Rittersdorf et al. ........... 435/11 |
| 5,460,974 A * | 10/1995 | Kozak et al. ................... 436/71 |
| 5,532,172 A | 7/1996 | Ziegenhorn et al. |
| 5,580,743 A | 12/1996 | Rittersdorf et al. |
| 5,597,532 A | 1/1997 | Connolly |
| 5,786,164 A | 7/1998 | Rittersdorf et al. |
| 5,807,696 A | 9/1998 | Miyauchi et al. |
| 5,814,472 A | 9/1998 | Miki et al. |
| 5,879,901 A | 3/1999 | Futatsugi et al. |
| 6,040,195 A * | 3/2000 | Carroll et al. ................. 436/514 |
| 6,171,849 B1 * | 1/2001 | Rittersdorf et al. ........ 435/283.1 |
| 6,214,570 B1 | 4/2001 | Rittersdorf et al. |
| 6,844,149 B1 * | 1/2005 | Goldman ........................ 435/4 |
| 2003/0224471 A1 * | 12/2003 | Jones et al. .................... 435/11 |

\* cited by examiner

*Primary Examiner*—Ralph Gitomer
(74) *Attorney, Agent, or Firm*—Patton Boggs LLP

(57) ABSTRACT

A multilayer test strip and method of using the test strip for determining concentration of HDL cholesterol in a whole blood sample. The inventive test strip includes a two-stage blood separation mechanism, including a first glass fiber matrix which separates most of the blood cells and an adjacent, second matrix preferably also containing glass fibers that separates the remainder of the blood cells. The second layer also precipitates and retains non-HDL cholesterol, thereby providing plasma that is substantially free of red blood cells and substantially free of non-HDL cholesterol to a reaction layer. Precipitation and retention on non-HDLs takes place by a vertical or dead-end filtration in a single layer. The reaction layer produces a color, the intensity of which is proportional to the concentration of HDL cholesterol in the blood sample which is applied to the test strip. Advantageously, the inventive test strip is a vertical flow device, which can be made more compact and operates more efficiently than a lateral flow device.

20 Claims, 23 Drawing Sheets

15 MICROLITER SAMPLE. 10 SECONDS

15 MICROLITER SAMPLE. 60 SECONDS

METHOD FOR DETERMINING HDL CONCENTRATION FROM WHOLE BLOOD OR PLASMA

CROSS REFERENCE TO RELATED APPLICATIONS

This application claims priority to U.S. Provisional Patent Application Ser. No. 60/342,790, filed on Dec. 21, 2001.

FIELD OF THE INVENTION

The present invention relates generally to testing of body fluids for concentration of cholesterol and more particularly to separating plasma or serum from whole blood and separating LDL and VLDL cholesterol from HDL cholesterol in the plasma.

BACKGROUND

The level of cholesterol in blood is a significant indicator of risk of coronary heart disease. "Total cholesterol" includes low density lipoproteins (LDL), very low density lipoproteins (VLDL) and high density lipoproteins (HDL). It is well established from epidemiological and clinical studies that there is a positive correlation between levels of LDL and VLDL cholesterol ("bad" cholesterol) and coronary heart disease and a negative correlation between levels of HDL cholesterol ("good" cholesterol) and coronary heart disease. The level of total cholesterol in blood, which is a measure of the sum total of HDL, LDL, VLDL and chylomicrons, is not generally regarded as an adequate indicator of the risk of coronary heart disease because the overall level of total cholesterol does not reveal the relative proportions of HDL, LDL and VLDL. To better assess the risk of heart disease, it is desirable to determine the amount of HDL cholesterol in addition to total cholesterol.

However, to measure HDL separately, two significant treatment steps to a whole blood sample are usually necessary. First, blood cells (especially erythrocytes) interfere with typical colorimetric tests and therefore must be separated from the whole blood sample to produce plasma or serum. Second, non-HDLs (i.e., LDL, VLDL and chylomicrons) must be removed from the plasma to be tested because reagents used to determine the level of HDL will also react with LDL and VLDL.

The conventional method of removing blood cells from whole blood is centrifugation. Centrifugation is a process step requiring time and a centrifuge, and it is therefore unacceptable for blood tests that are conducted in many physicians' offices, on-site testing by medical technicians, and testing by patients at home. Further, centrifugation can cause problems with separating supernatant and blood cake.

A significant advance to the field of diagnostic devices was ushered in with the discovery by Vogel, et al. (U.S. Pat. No. 4,477,575) in the early 1980's that glass fibers could be used to separate red cells from whole blood. Because of optical and chemical interference from hemoglobin in red cells, the only material that could be measured in whole blood at that time was glucose, using early test strips that required the red cells to be washed or wiped off after glucose had permeated a paper-based matrix (for example, U.S. Pat. No. 3,298,789 to Mast). Glass fibers separate red blood cells by physical and chemical adhesion of the cell surface to the glass fibers. Even today, however, the precise nature of the attraction between glass fibers and red blood cells is not clearly understood. Weak chemical bonding, van der Waals forces, hydrogen bonding or other intermolecular forces may have a role in this attraction.

The discovery that glass fibers separate blood cells, however, allowed, for the first time, measurement of cholesterol and other blood components in a doctor's office instead of a reference laboratory, and the first commercial device to utilize this technology was Boehringer Mannheim's (now Roche Diagnostics) Reflotron® instrument. This advance was subsequently incorporated into test strips, allowing blood testing at home.

Notwithstanding the significant achievement of the '575 patent, applicants have found that commercially available test strips embodying the '575 patent and its progeny are "lateral flow devices." The defining feature of a lateral flow device is the presence of a sample application point that is laterally offset (along the axis of the test strip) from the sample reading area of the test strip. For example, certain commercially available devices that appear to embody the teachings of the '575 patent include a blood application area at one end of the elongated test strip and a test reading area at the other end. A whole blood sample is deposited at one end of the glass fiber blood separation layer, and plasma migrates to the other end at a greater rate than do red blood cells. However, it has been experimentally determined by applicants that red blood cells from the sample that is placed on the disclosed glass fiber matrix eventually migrate tangentially across the fiber matrix, albeit at a slower rate than plasma. Further, some hemolysis of the erythrocytes eventually occurs in the glass fiber layer.

Furthermore, applicants have found that some commercially available total cholesterol test strips are configured such that the reaction layer is not initially in contact with the glass fiber blood separation layer. Instead, the reaction layer is not brought into fluid-conveying contact with the glass fiber layer until the glass fiber layer is filled with plasma. This happens at a predetermined time after an adequate amount of plasma, but not red blood cells, has migrated laterally to a designated location on the glass fiber layer. Timing is thus important to the successful use of such test strips. If the reaction layer is brought into contact with the glass fiber layer too soon after depositing the blood sample on the strip, not enough plasma will have migrated to the designated area of the strip and the analyte concentration determined may be inaccurately low. On the other hand, if the reaction layer and glass fiber layer are not brought into contact soon enough, hemolyzed and intact red blood cells will migrate to the test area and interfere with the color to be measured from the reaction. Applicants have found these commercially available test strips to be highly accurate when used as directed. However, it would be desirable to avoid the process step of bringing the test layer into contact with the blood separation layer.

Another blood separation scheme is disclosed in U.S. Pat. No. 5,135,716 (Thakore) and the abandoned application from which it claims priority. The device described in the '716 patent is also a lateral flow device but operates differently than the glass fiber matrices described in the '575 patent. The '716 device purports to employ an industrial "cross-flow" or "tangential filtration" technique on a miniature scale. The blood sample is applied to one end of a physical transport medium and is moved laterally thereby, along the underside of a microporous plasma separation membrane. Blood is separated at the bottom surface of this microporous plasma separation membrane, and clean plasma is obtained on the top side of the membrane. The transport medium provides the driving force for lateral movement of blood, such that blood is swept across the underside of the microporous plasma separation membrane, thereby cleaning it and preventing it from clogging with red blood cells. However, to Applicants' knowledge, there has never been a commercial test strip produced or sold under the '716 patent, likely because the blood separation technology described in the patent, among other things, is simply unworkable.

Another alternate approach to centrifugation to separate blood cells is disclosed in U.S. Pat. No. 5,876,605 (Kitajima et al.). The method involves mixing an aqueous solution of an inorganic salt or an amino acid or salt thereof with whole blood in an amount 20% or less of the whole blood volume and then filtering the whole blood to remove blood cell components. While satisfactory results are apparently achieved with the wet chemistry method disclosed, the '605 patent teaches that the technique cannot be successfully adapted to dry test layers such as glass fiber matrices. '605 patent, column 11, lines 1–30.

Test strips for precipitation and separation of non-HDL cholesterol from HDL cholesterols in a plasma sample are disclosed by U.S. Pat. No. 5,426,030 (Rittersdorf et al.) and its progeny. This separation technology involves a test strip with two layers in contact with one another. The first layer is made from glass fibers in the form of fleeces, the glass fibers having a diameter from 3 to 100 µm. The first layer is hydrophilic, having a thickness between 20–250 µm and pore sizes between 0.2–20 µm, and is impregnated with a precipitating agent that precipitates non-HDLs but not HDLs. The second layer is preferably a mesh glass fiber layer with fibers of a diameter of 0.2 to 10.0 µm. Precipitation of non-HDL cholesterols occurs in the first layer and separation of the non-HDL precipitants from the plasma occurs in the second layer.

U.S. Pat. No. 5,135,716 (Thakore), discussed above, discloses a multilayer strip, two of such layers being used for precipitating and then separating non-HDLs from plasma, respectively. The '716 patent also suggests that precipitation and separation of non-HDLs from plasma can be carried out in a single "asymmetric" carrier layer. The asymmetric layer essentially operates as two layers, in that the top portion of the layer includes large pores to allow fluid movement and precipitation, whereas the bottom portion of the layer includes smaller pores to trap the precipitants. Applicants have found that this disclosure does not rise beyond mere speculation, in that no examples or enabling disclosure of the single asymmetric layer technology to separate non-HDLs from plasma are found in the '716 patent.

Yet another elaborate device to measure the concentration of HDL cholesterol from a whole blood sample is disclosed in U.S. Pat. No. 5,213,965 (Jones) and other related and commonly assigned patents. The device includes a well in which the whole blood sample is deposited and then drawn through a capillary to a sieving pad made of fibrous material. The sieving pad achieves initial separation of blood cells from plasma on the basis of the blood cell's slower migration rate therethrough. The sieving pad is covered with a microporous membrane which further filters blood cells. Covering the microporous membrane is a reagent reservoir membrane containing precipitating agents for non-HDLs. On top of and extending laterally beyond the reagent reservoir is an elongate matrix which distributes the sample laterally after it leaves the reservoir. Finally, one or more test pads are positioned above and biased apart from the elongate matrix. Plasma exits the filtering membrane and enters the reagent reservoir where non-HDLs are precipitated. The plasma and non-HDL precipitates then flow from the reservoir and migrate laterally through the elongate matrix.

Undesirably, the device disclosed by the '965 patent relies upon not one, but two, separate chromatographic operations, the first being blood separation in the sieving pad, and the second being separation of non-HDLs across the elongate matrix. Proper timing is crucial to these chromatographic operations. Further, the device disclosed by the '965 patent is undesirably complex. For example, it requires a well, a capillary tube, two layers to separate blood cells, and two layers to precipitate and then separate non-HDLs. Finally, the test pads must be kept spaced apart from the elongate matrix until the entire operation is properly timed, whereupon the test plate having the test pads thereon can be depressed against the elongate matrix. Of course, depressing the test pad creates yet another undesirable process step and introduces further potential for error.

U.S. Pat. No. 5,460,974 (Kozak et al.) discloses a test device for measuring HDL cholesterol. The device relies upon a blood separation layer having incorporated therein about 25 to about 250 units of an agglutinin, about 50 to about 150 NIH units of a coagulant or a mixture thereof to agglutinize or coagulate the cellular components of the undiluted whole blood sample. The plasma is then passed into an adjacent layer by gravity to separate the LDL and VLDL fractions from the plasma, followed by a layer which filters the non-HDLs. Applicants have found that using an agglutinin or a coagulant to separate blood cells is undesirable because it affects the measured test result.

It is desirable to avoid the lateral flow schemes, chromatographic operations, complex devices and the timing operations that are required for blood cell separation in the patents discussed above. It would also be desirable to achieve a blood separation mechanism that is more efficient and dependable than those listed above. It is also desirable to simplify non-HDL separation from plasma. Generally, it is desirable to provide a test strip for measuring concentration of HDL cholesterol that is more reliable, economical and easier to use than the prior art devices discussed above.

SUMMARY OF THE INVENTION

The present invention is a multilayer vertical flow test strip and method for using the same to measure HDL concentration from whole blood or plasma. The test strip includes a two stage blood separation mechanism, wherein a first glass fiber matrix separates most of the blood cells and an adjacent, second matrix, also preferably containing glass fibers, separates the remainder of the blood cells. The second layer also precipitates and retains non-HDL cholesterol, thereby providing plasma that is substantially free of red blood cells and free of non-HDL cholesterol to a reaction layer that produces a colored response in proportion to the concentration of HDL cholesterol in the sample.

In one form thereof, the present invention provides a method of determining concentration of HDL cholesterol in a whole blood sample with a dry phase test strip. The method comprises depositing the whole blood sample at an application area of the test strip, contacting the whole blood sample with a first test layer of the test strip and separating and retaining a first portion of red blood cells from the blood sample in the first test layer. Fluid containing a remaining portion of red blood cells is then passed to a second layer of the test strip, the second layer being adjacent to and in contact with the first test layer. In the second layer, the remaining portion of red blood cells is separated and retained, and non-HDL cholesterol is also precipitated and retained, thereby producing plasma that is substantially devoid of red blood cells and non-HDL cholesterol. The plasma is passed from the second layer to a reaction layer of the test strip, the reaction layer being adjacent to and in contact with the second test layer. The reaction layer produces a colored response proportional to the concentration of HDL cholesterol in the whole blood sample.

In a preferred form, the first layer is impregnated with a salt such as sodium chloride (NaCl) and a sugar such as sorbitol. More preferably, the second layer is impregnated with phosphotungstic acid (PTA) to precipitate the non-HDLs.

While the exact mechanism by which this inventive test strip works is still uncertain, the applicants have made some amazing discoveries since filing provisional application 60/342,790, from which this application claims priority. Surprisingly, and quite contrary to what was initially believed, the first glass fiber matrix does not provide complete separation of blood. Instead, most of the red blood cells are retained in the first glass fiber layer, but the remainder of red blood cells is passed to and retained in the second glass fiber layer. This is quite an unexpected result because the second glass fiber layer is impregnated with phosphotungstic acid, which is known to hemolyze red blood cells. Hemolyzed red blood cells would be expected to migrate to the reaction layer and interfere with the test result. Quite surprisingly, however, the test results have been found to be quite accurate, notwithstanding that red blood cells are passed to the second glass fiber matrix.

One significant advantage of the blood separation mechanism of the present invention is that it is a vertical flow device, which consequently works in a dead-end or vertical flow format, which is in stark contrast to the prior art lateral flow devices noted above. Of course, there is fluid movement, especially spreading, in all directions in applicants' inventive test strips. Significantly, however, there is no need to allow for any net lateral movement of fluid from one side of a layer to the other, as required by prior art devices. Advantageously, applicants' test strip can be made more compact because the large surface area of transport media needed in prior art devices for lateral movement has been eliminated. In other words, the test layers can be vertically aligned with one another and made smaller, thereby enabling a smaller and more compact test strip which requires a smaller blood sample.

Another advantage of the present invention is that it avoids the time-dependent chromatographic flow schemes required by prior art test strips. As noted above, certain prior art test strips require that the test layer and blood separation layer are maintained spaced apart until a predetermined time at which plasma but not red blood cells has migrated to the contact area. With the present invention, this is unnecessary. All test layers are always positioned together. There are no moving parts in applicants' test strips. In applicant's test strips, separation of blood is achieved in a direction that is substantially normal (i.e., orthogonal or perpendicular), not tangential, to the plane of the test layers.

Surprisingly, it has been found that both precipitation and retention of non-HDLs can be conducted in a single, uniform layer. This is indeed remarkable in light of the teachings of the prior art that are replete with a two-layer or two-step technology, precipitation taking place in the first layer and separation in the second. (See, e.g., U.S. Pat. Nos. 5,426,030; 5,580,743; 5,786,164; 6,171,849; 6,214,570; 5,451,370; 5,316,916; 5,213,965; and 5,213,964.) The advantages of eliminating an entire layer from a multilayer test strip are manifest. The strip is less expensive because material costs are eliminated and, of course, the strip is easier and quicker to assemble.

BRIEF DESCRIPTION OF DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Definitions

"HDL" refers to high density lipoprotein.

"LDL" refers to low density lipoprotein.

"VLDL" refers to very low density lipoprotein.

"Non-HDL" refers to LDL, VLDL and chylomicrons, i.e., lipoproteins other than HDL that will react with a conventional cholesterol reaction membrane.

"PTA" refers to phosphotungstic acid.

"Plasma" refers to the non-cellular portion of blood from which cellular components such as red blood cells are excluded.

"Serum" technically differs from plasma, in that it does not include fibrinogen. However, for purposes of this application "serum" and "plasma" are sometimes used interchangeably.

"Vertically aligned" refers to a stack of two or more test layers used in a dry phase test strip, the layers being substantially coextensive with and aligned with one another in a stack such that no layers protrude significantly from any of the other layers.

Test Device

Figure 1:
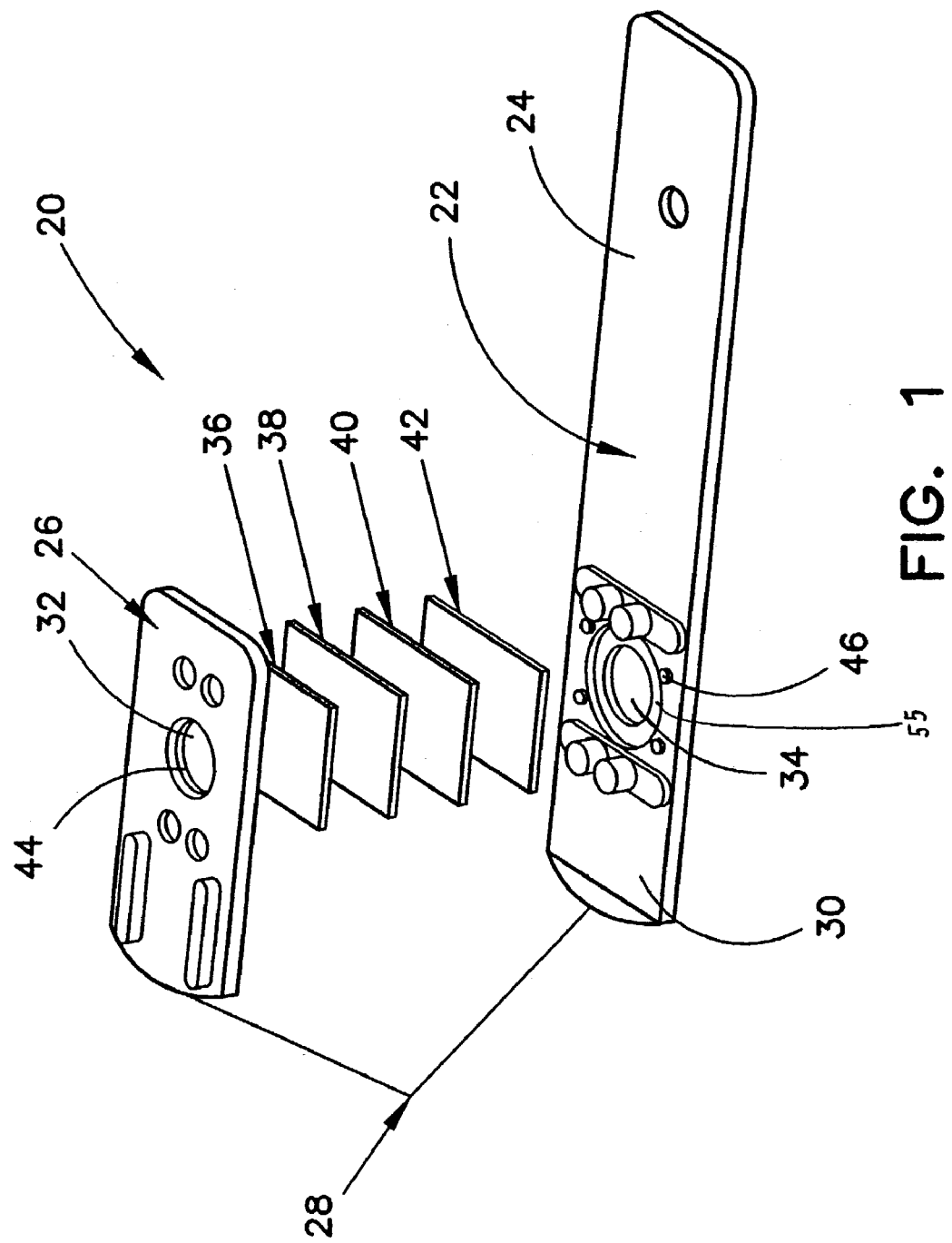
FIG. 1 is an exploded perspective view of a test strip in accordance with the present invention used to determine the concentration of HDL cholesterol in a sample of whole blood.

Referring now to FIG. 1, test strip 20 includes test strip holder 22 which is preferably formed by injection molding. Test strip holder includes handle 24 and end portion 26 which is preferably hingedly attached by hinge portion 28 to second end portion 30, shown exploded away in FIG. 1. Portion 26 is foldable about hinge portion 28 over portion 30 as shown. End portion 26 includes an opening 32 while end portion 30 includes a complementary spaced opening 34. When end portion 26 is folded over end portion 30, openings 32 and 34 are aligned. In its folded position, opening 32 in holder 22 defines an application window for depositing a body fluid sample while opening 34 defines a test reading window in which optoelectronic measurements of chemistry test reactions are conducted.

A test strip holder essentially the same as that described with reference to FIG. 1 is shown and described in U.S. Pat. No. 5,597,532, the disclosure of which is hereby incorporated by reference. The test strip holder is not critical to the invention and other suitable embodiments of a test strip holder are contemplated by this invention. The particular test strip described herein is suitable for use with an optoelectronic instrument sold under the trademark Cardio Chek, commercially available from Polymer Technology Systems, Inc., Indianapolis, Ind.

Figure 2:
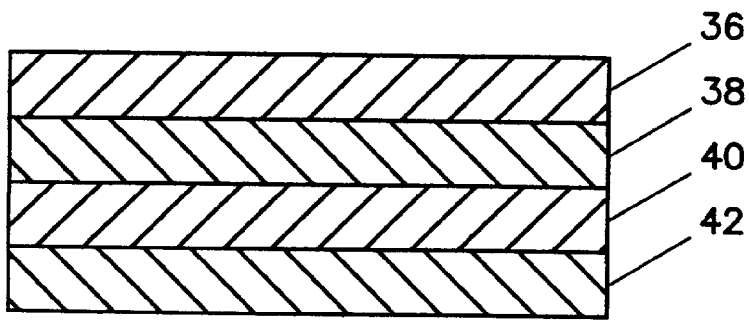
FIG. 2 is a sectional view illustrating the layers of the test strip of FIG. 1.
Figure 21:
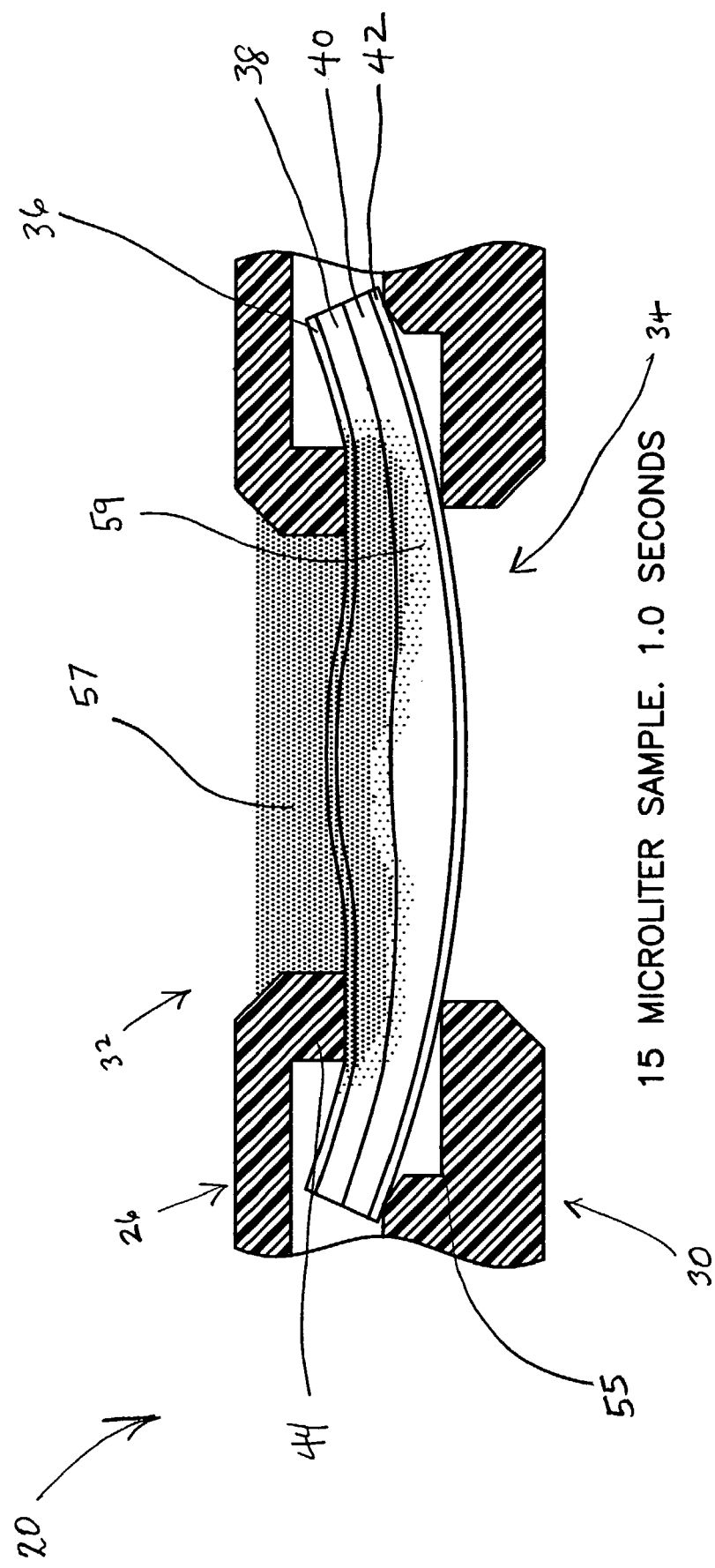
FIG. 21 is a cross sectional view of a test strip in accordance with the present invention showing movement of blood and plasma at 1.0 seconds after the blood sample has been applied to the strip.

Turning now to FIG. 1 and FIG. 2, there are four layers held within test strip holder 22 without requiring adhesives. Unlike the teachings of the '532 patent, it has been found that it is desirable to exert a compressive force upon the layers between end portion 26 and end portion 30. The proper compressive force exerted upon the layers is a design variable that can be adjusted by (1) adjusting the available space between ends 26 and 30 when the strip is snapped together; (2) adjusting the size and length of rim 44, which rim depends downwardly from opening 32 and engages the top layer held between ends 26 and 30; (3) adjusting the size of protuberances 46, which also engage the layers; and (4) adjusting the depth of shelf 55. A desirable compressive force to be exerted on the test layers by the test strip reduces the height of the stack of layers by about twenty percent (20%) from the height the layers would occupy if no compressive force were exerted. The compression is obviously more extensive proximate boss or rim 44 (see FIGS. 21–24). It is believed that compressing the layers removes air pockets within the test matrix and thereby improves the speed with which the physical and chemical processes take place. This, in turn, improves the precision of the test. Compression is effectuated by sandwiching the stack of layers between downwardly depending rim or boss 44 and shelf 55 (FIGS. 1 and 21). This compression causes the stack of layers to form the curved profile shown in FIGS. 21–24.

The top layer 36 is a disbursement or spreader mesh layer formed of, for example, woven materials such as polyester or cotton, non-woven fabric, gauze or monofilament yarn. One suitable material for spreader layer 36 is a Sefar PeCap (07-17/9) available from Sefar American, Inc., DePew, N.Y. Layer 36 provides rapid and even disbursement of a body fluid such as whole blood or plasma. It has been found that test strip 20 works without layer 36, but layer 36 is desirable because it provides a more uniform distribution of blood to the subjacent layer and the test results vary less when the spreader layer is used.

Beneath and in fluid communication with disbursement or spreader layer 36 is layer 38, whose composition and preparation are described in greater detail below. Layer 38 separates blood cells (erythrocytes) from whole blood and passes a fluid containing a remaining portion of blood cells therethrough. It has been experimentally found that about 80%–90% of red blood cells are retained within layer 38 during the duration of the test period. Beneath and in fluid communication with layer 38 is layer 40, whose composition and preparation are described in greater detail below. Bottom layer 42 is a reaction layer in which dry chemicals and reactants are contained for generating a visible color change in the presence of cholesterol, and layer 42 is positioned beneath and in fluid communication with layer 40 as shown. It may be desirable in some circumstances to provide additional layers between some of the aforementioned layers, for example, to improve absorption and fluid communication between layers.

Blood Separation

Layer 38 is generally a glass fiber matrix. A suitable commercial material for layer 38 is Ahlstrom Grade 144, thickness 0.378 mm, available from Ahlstrom Filtration, Inc., Mt. Holly Springs, Pa. Other glass fiber matrices could be substituted. Generally, layer 38 should include glass fibers with a diameter of 0.5 to 2 microns and a density of 0.1 to 0.5 g/cm$^3$, more preferably 0.1 to 0.2 g/cm$^3$. Layer 40 is also preferably a randomly dispersed glass fiber matrix. In the illustrated embodiment, layer 40 includes a blend of glass microfiber, cellulose fiber, and synthetic staple fiber. The glass microfiber component consists of alkali-containing or alkali-free borosilicate glass or pure quartz fibers, having a mean fiber diameter of 0.3 to 0.7 micrometers. The bulk density of the glass microfiber component is less than 0.1 g/cm$^3$, and is typically about 0.05 g/cm$^3$. One suitable membrane for layer 40 is CytoSep® grade 1660 membrane, 12.9 mils thick, available from Pall Specialty Materials, Port Washington, N.Y. Another suitable membrane for layer 40 is paper grade 595, 0.180 mm (7.1 mil) thick, available from Schleicher & Schuell, Keene, N.H.

Surprisingly, the inventors of the present invention have found that separation can be improved by impregnating layer 38 with a salt and a sugar. Without wishing to be tied to any specific theory, it is believed that the ions from the salt, when acting upon the aqueous blood sample, cause water in the blood cells to be discharged into the plasma, thereby decreasing the volume of the red blood cells. This decrease in red blood cell volume can be crudely likened to a grape that when dehydrated contracts into a raisin. Just as a raisin is smaller, more durable and has a skin that is less flexible than a grape, red blood cells acted on by the salt in layer 38 become smaller, more durable and their membranes less flexible. Even though the erythrocytes acted upon by the salt are smaller, they are less likely to deform and thus less likely to pass through the glass fiber matrix. Further, hemolysis (destruction of red blood cells) is reduced by the action of the salt. Also, as discussed above, it has been widely recognized that red blood cells have an affinity for glass fibers. This affinity appears to be enhanced by impregnating the layer with salt.

The amount of salt used to impregnate layer 38 must be relatively small, typically on the order of 1% by weight on a wet basis of the solution used to impregnate layer 38. If too much salt is added to the impregnating solution, the red blood cells can rupture in layer 38 due to a high osmotic pressure difference between the inside and outside of the red blood cells. If the amount of salt added is too small, the desired effect imparted to the red blood cells will not be achieved. Salt concentrations in the range of 0.5% to 3% are preferable. While the examples disclosed hereinbelow employ NaCl as the preferred salt, it is envisaged that other salts would also work well. Suitable salts would include KCl, MgCl$_2$, CsCl$_2$, Li$_2$SO$_4$, CaCl$_2$, Rb$_2$SO$_4$ and CsSO$_4$. Amino acids such as Gly, Ala, Asp, Glu and glycinamide asparagine may also perform suitably.

It is also important that membrane 38 be impregnated with a sugar such as sorbitol, which acts as a wetting agent which increases the rate and extent of fluid movement through layer 38. Without sufficient movement of fluid within layer 38, red blood cells can collect and agglomerate and block plasma from passing through membrane 38, which in turn causes white spots on reaction layer 42. These spots can interfere with the reading of the test instrument.

Another important benefit of the enhanced speed of movement from the wetting agent relates to the fact that intact blood can eventually find its way around the layers in the test device and onto the reaction layer. This typically results in dark blue spots on the reaction layer caused by components of hemolysed blood. However, with a good wetting agent like sorbitol, the reaction is over and the result of the test recorded several minutes before this type of interfering effect takes place.

While sorbitol is the preferred wetting agent in accordance with this invention, other wetting agents could be substituted. For example, it is anticipated that mannitol would also perform suitably in the same concentrations as sorbitol.

The inventors have found that layer 38, by itself, does not retain 100% of the blood cells. Instead, it has been found that layer 40 also contributes to blood separation. The fluid passed to layer 40 has about 80%–90% of its red blood cells removed. The percentage of blood cells retained in layer 38 can vary depending upon parameters such as hematocrit of the blood sample.

As alluded above, the inventors of the present invention have discovered that blood separation in the novel HDL test strip of the present invention involves a two-stage, two-layer mechanism. The first glass fiber layer 38 is comprised of a more open matrix having larger glass fibers that are more dense than those in layer 40. This more open matrix allows greater movement of blood which is important for a whole blood sample. By contrast, glass fiber layer 40 includes small glass fibers having lower density and also includes, as noted above, cellulosic fiber and synthetic fibers disbursed throughout the matrix. Thus, layer 40 is a more tightly packed matrix having smaller nominal pore size, but therefore being able to trap the remainder of the red blood cells therein. The applicants have found that such a two-layer, two-step blood separation process in the present invention allows for very accurate test results. Since the present invention is a vertical flow device, one of ordinary skill in the art would expect that blood separation would be more difficult to achieve in a single layer, in view of the much smaller available volume through which the blood flows as compared to a lateral flow device.

Single Layer Precipitation and Separation of Non-HDLs

As noted above, the prior art generally teaches that two layers and two associated process steps are necessary to precipitate and separate non-HDLs from plasma. According to the prior art approach, precipitation of non-HDLs is carried out in the first layer and the precipitants then pass through this first layer to a second layer. In the second layer, the precipitants' migration is slower than that of plasma, and the plasma reaches the test membrane before the precipitants. See, e.g., U.S. Pat. Nos. 5,426,030; 5,580,743; 5,786,164; 6,171,849; 6,214,570; 5,451,370; 5,316,916; 5,213,965; and 5,213,964. By contrast, the inventors of the present invention have found that separation of non-HDLs from HDLs can be achieved in a single, substantially uniform layer 40 by, among other things, improving blood separation in layer 38, choosing a sufficiently thick layer 40, and treating the layers such that sufficient fluid movement is achieved therethrough.

Further, and quite remarkably, applicants' strip is designed such that precipitation and separation take place in a direction that is substantially normal to the plane established by layer 40. That is, while fluid movement occurs in all directions within layer 40, there is no significant net lateral migration of fluid from one side of layer 40 to the other. Indeed, quite unlike the prior art noted above, the present invention does not incorporate or rely on different migration rates of plasma and precipitated non-HDLs across layer 40. This is because fluid transport is through layer 40, not across it. Thus, it can be appreciated that blood separation and separation of precipitated non-HDLs both occur vertically, in a direction that is perpendicular to the plane of the vertically aligned test layers. This is a significant advantage, in that the test strip can be configured compactly in a vertically aligned stack of layers.

Vertical flow through the layers is inherently more efficient than lateral flow across the length of the layers. However, the design hurdle has been to configure a test strip that can perform multiple chemical and physical functions, viz., separation of blood, precipitation and retention of non-HDL cholesterol and reading a test result all in a vertical flow format. When fluid is traveling through the layers rather than across them, simply not much volume of the individual test layers that is utilized, in stark contrast to lateral flow. Thus, accomplishing both precipitation and retention of the precipitation in a vertical flow format is a significant achievement.

Layer 40 is substantially uniform throughout or symmetric. That is to say, while the matrix of layer 40 includes pores of different sizes, the matrix is consistent throughout the entire layer. Asymmetric layers with varying pore size such as that speculated in U.S. Pat. No. 5,135,176, wherein precipitation occurs primarily in the top part of the layer and separation occurs at the bottom part of the layer, are unnecessary with the present invention.

To achieve precipitation and separation of non-HDLs in a single layer, it is important that layer 40 be impregnated with a suitable precipitating agent in a specified concentration. It is known that certain polyanions in combination with bivalent cations are particularly suitable as precipitating agents in wet chemistry techniques. Examples of these include combinations of heparin and manganese (II) chloride, dextran sulphate and magnesium chloride, polyethylene glycol (PEG), or phosphotungstic acid (PTA) and magnesium chloride. In wet chemistry techniques, each polyanion can theoretically be combined with any of the three cations ($Mg^{2+}$, or $Mn^{2+}$, or $Ca^{2+}$).

However, the inventors of the present invention have found that the capacity to precipitate lipoproteins and retain them within the same layer in which they are precipitated varies with the choice of precipitating agent. In accordance with the present invention, it has been found that phosphotungstic acid (PTA) combined with magnesium sulfate performs better than other precipitating agents. It is preferable to use PTA in the amount of 1–4.5% weight percentage on a wet basis of the solution to impregnate layer 40.

It is known that PTA hemolyzes red blood cells, as noted in U.S. Pat. No. 5,135,716 (Thakore). Theoretically, then, one of ordinary skill in the art would expect that the red blood cells that escape layer 38 and pass into layer 40 would be hemolyzed by the PTA in layer 40 and thus more readily pass into reaction layer 42, thereby interfering with the colored test result. Applicants initially believed that the present invention worked well because substantially no red blood cells escape layer 38 and thus hemolysis due to PTA does not occur. As note above, however, it has recently been discovered that layer 38 only separates 80–90% of the red blood cells. Thus, it is quite remarkable and surprising that the red blood cells that are retained by layer 40 do not cause the undersirable effect just noted.

It is also important to choose a suitable wetting agent for layer 40. Applicants have found that a sugar such as sorbitol is suitable in a concentration on the order of 0.5% to 2% by weight on a wet basis of the solution to impregnate layer 40.

Figure 3:
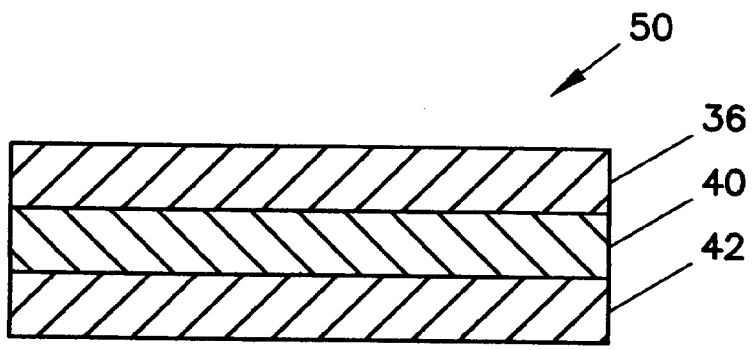
FIG. 3 is a sectional view of a test strip in accordance with an alternate embodiment of the present invention used to determine the concentration of HDL cholesterol in a sample of serum or plasma.

It is to be understood that layer 40 can be used in a test device to test samples of plasma or serum from which blood cells have already been removed by, for example, centrifugation. With reference to FIG. 3, plasma or serum is deposited on spreader layer 36 of test device 50, which diffuses and passes same therethrough to layer 40. In layer 40, non-HDLs are precipitated and retained, while HDLs remain in solution and pass through layer 40 to reaction layer 42. In reaction layer 42, HDL cholesterol produces a colored response, the intensity of the color being proportional to the concentration of HDL.

Cholesterol Detection

Selection of the cholesterol detection membrane is not critical provided that substantially pure plasma, devoid of non-HDLs, is provided thereto. In this connection, the present invention increases the amount of alternate choices for the cholesterol detection membrane because of the high quality and purity of the fluid provided to it. One suitable membrane 42 is a Pall Biodyne A Nylon 6,6 Membrane, which has a pore rating of 0.45 microns and a thickness of 5.5–6.5 mm.

It has been found that CHAPS, or 3-[(3-cholamidopropyl) dimethylammonio]-1-propanesulfonate, available from Research Organics, Cleveland, Ohio, is preferable over cholic acid that is typically used to impregnate prior art reaction membranes. Cholic acid acts as an activator for cholesterolase in the enzyme. CHAPS performs two functions. It acts as a detergent, and because it is structurally similar to cholic acid, CHAPS also acts as an activator.

CHAPS is more soluble and also more easily reconstituted by plasma than is cholate. CHAPS can thus more readily enhance pancreatic esterase activity than cholate. Consequently, more chromogen is produced and the dynamic range of the test is increased. Since CHAPS is more readily resolubilized than cholate, the diagnostic test strips will have greater precision because the CHAPS will be more uniformly distributed throughout the reaction membrane 42 almost immediately after the addition of blood to strip 20.

Furthermore, because of its different properties, CHAPS was found to be more compatible than cholate with a larger number of different chromogenic systems, particularly the Trinder systems. In solutions made with cholate, for example, 4-aminoantipyrine would not remain in solution. Since CHAPS is a more acidic surfactant than cholate, it is able to be solubilized and remain in solution at a lower pH than cholate. This allows the pH to be lowered from 6.8 to 6.0, thereby eliminating uric acid interference.

The following examples will enable one of ordinary skill in the art to fully practice the present invention. Examples 1–7 illustrate preparation and alternate materials for different layers of test apparatus 20 and assembly of the test apparatus, itself. Examples 8–14 illustrate different embodiments of a test apparatus 20 using the solutions and alternate materials from examples 1–7.

EXAMPLE 1

Preparation of Layer 38

Ahlstrom Grade 144 glass fiber membrane having a thickness of 0.378 mm was impregnated with a solution with the following composition:

| | |
|---|---:|
| D.I. Water | 800 g |
| NaCl | 10 g |
| Sorbitol | 50 g |
| Citric Acid | 0.21 g |
| pH 4.2–4.4 (adjusted with HCl or NaOH) | |
| Q.S. to 1000 mL with D.I. Water | |

The membrane was placed on a conveyor and submersed in a re-circulating bath of the above impregnation solution at a rate of 0.5 ft/min. It then entered a tunnel of blowing warm air (98°–106° F.) and low humidity (less than 5% Relative Humidity) to dry completely. In another test run, Schleicher and Schuell 33 Glass, a borosilicate glass with acrylic latex binder with a thickness of 0.370 mm was substituted for the Ahlstrom Grade 144 glass fiber membrane.

EXAMPLE 2

Preparation of Blood Separation Membrane 38

The same fiber layers were used as in example 1, except the sorbitol component of the impregnation solution was changed as indicated below:

| | |
|---|---:|
| Water, D.I. Purified | 800 g |
| NaCl | 10 g |
| Sorbitol | 75 g |
| Citric Acid | 0.21 g |
| pH 4.2–4.4 | |
| Q.S. to 1000 mL with D.I. Water | |

Schleicher and Schuell Grade 30, 31, and 33, and Whatman GF/DVA, GF/D, F145-02, F147-11, F147-14, and 487-09 were also used. (See Examples 15 et seq.)

EXAMPLE 3

Preparation of Cholesterol Detection Membrane 42

A Pall Biodyne A Nylon 6,6 Membrane with a pore rating of 0.45 microns and a thickness of 5.5–6.5 mm was impregnated with a solution with the following composition:

| | |
|---|---:|
| D.I. Water | 200 g |
| Triton X-100 | 0.771 g |
| Cholesterol Foundation** | 532 g |
| BSA, Std. Powder | 13.88 g |
| 10% Gantrez AN-139 (w/v) | 95.61 g |
| CHAPS | 19.82 g |
| Sucrose | 37.01 g |
| pH 4.9–5.1 | |
| Potassium Ferrocynanide | 0.116 g |
| TOOS | 0.37 g |
| MAOS | 4.63 g |
| Cholesterol Oxidase | 148 KU |
| Peroxidase | 462.6 KU |
| Bovine Cholesterol Esterase | 92.5 KU |
| LPL-311 Cholesterol Esterase | 240.6 KU |
| 4-Amino anti-pyrine | 4.163 g |
| Final pH 5.3–5.5 | |
| Q.S. to 1000 mL with D.I. Water | |

The membrane was submersed in a re-circulating bath of impregnation solution at a rate of 1 ft/min. It then entered a tunnel of blowing warm air (98°–106° F.) and low humidity (<5% RH) to dry completely. The Cholesterol Foundation indicated above with ** was made up of the following constituents:

| | |
|---|---:|
| D.I. Water | 800 g |
| Sodium Citrate, dihydrate | 30 g |
| PVP K-30 | 60 g |
| Benzoic Acid | 2 g |
| BSA, Std. Powder | 4 g |
| EDTA, disodium, dihydrate | 1.47 g |
| pH 5.4–5.6 | |
| Q.S. to 1000 mL with D.I. Water | |
| Catalase | 0.05 KU |

EXAMPLE 4

Preparation of HDL Fractionation Membrane (Layer 40)

A Schleicher and Schuell Grade 576 calendered, hardened, low ash filter paper with a thickness of 0.125 mm was impregnated with a solution with the following composition:

| | |
|---|---:|
| D.I. Water | 800 g |
| Magnesium Sulfate | 5 g |
| Phosphotungstic Acid | 10 g |
| Sorbitol | 10 g |
| pH 6.4–6.6 | |
| Q.S. to 1000 mL with D.I. Water | |

The membrane was submersed in a re-circulating bath of impregnation solution at a rate of 0.5 ft/min. It then entered a tunnel of blowing warm air (98°–106° F.) and low humidity (<5% RH) to dry completely.

EXAMPLE 5

Preparation of HDL Fractionation Membrane 40

The following impregnation solution was used in the procedure analogous to Example 4, except the amount of PTA was varied as indicated:

| | |
|---|---:|
| D.I. Water | 800 g |
| Magnesium Sulfate | 5 g |
| Phosphotungstic Acid | 20 g |
| Sorbitol | 10 g |
| pH 6.4–6.6 | |
| Q.S. to 1000 mL with D.I. Water | |

EXAMPLE 6

Preparation of HDL Fractionation Membrane 40

The following impregnation solution was used in the procedure set forth in Example 4, except the amount of PTA was changed as indicated:

| | |
|---|---:|
| D.I. Water | 800 g |
| Magnesium Sulfate | 5 g |
| Phosphotungstic Acid | 45 g |
| Sorbitol | 10 g |
| pH 6.4–6.6 | |
| Q.S. to 1000 mL with D.I. Water | |

The impregnating compositions listed above in Examples 4–6 were also used with Cytosep® Grade 1660 and Grade 1661 membranes, which are a blend of natural and synthetic fibers with a thickness of 12.9 mm and 7.1 mm, respectively, and Schleicher and Schuell Grade 595, which is a pressed paper with a thickness of 0.180 mm.

EXAMPLE 7

Assembly of Test Apparatus 20

The membranes were placed in the following order between the pins in the test strip holders: Bottom layer 42 (reagent impregnated cholesterol membrane), then the non-HDL capture layer 40, then blood separation membrane 38, and finally the mesh screen or spreader layer 36. The test strip holder 22 was then folded and pressed to ensure closure. The strip holder was staked using a cold stake press, and then cut to individual strips and placed in vials with desiccant.

EXAMPLE 8

Figure 4:
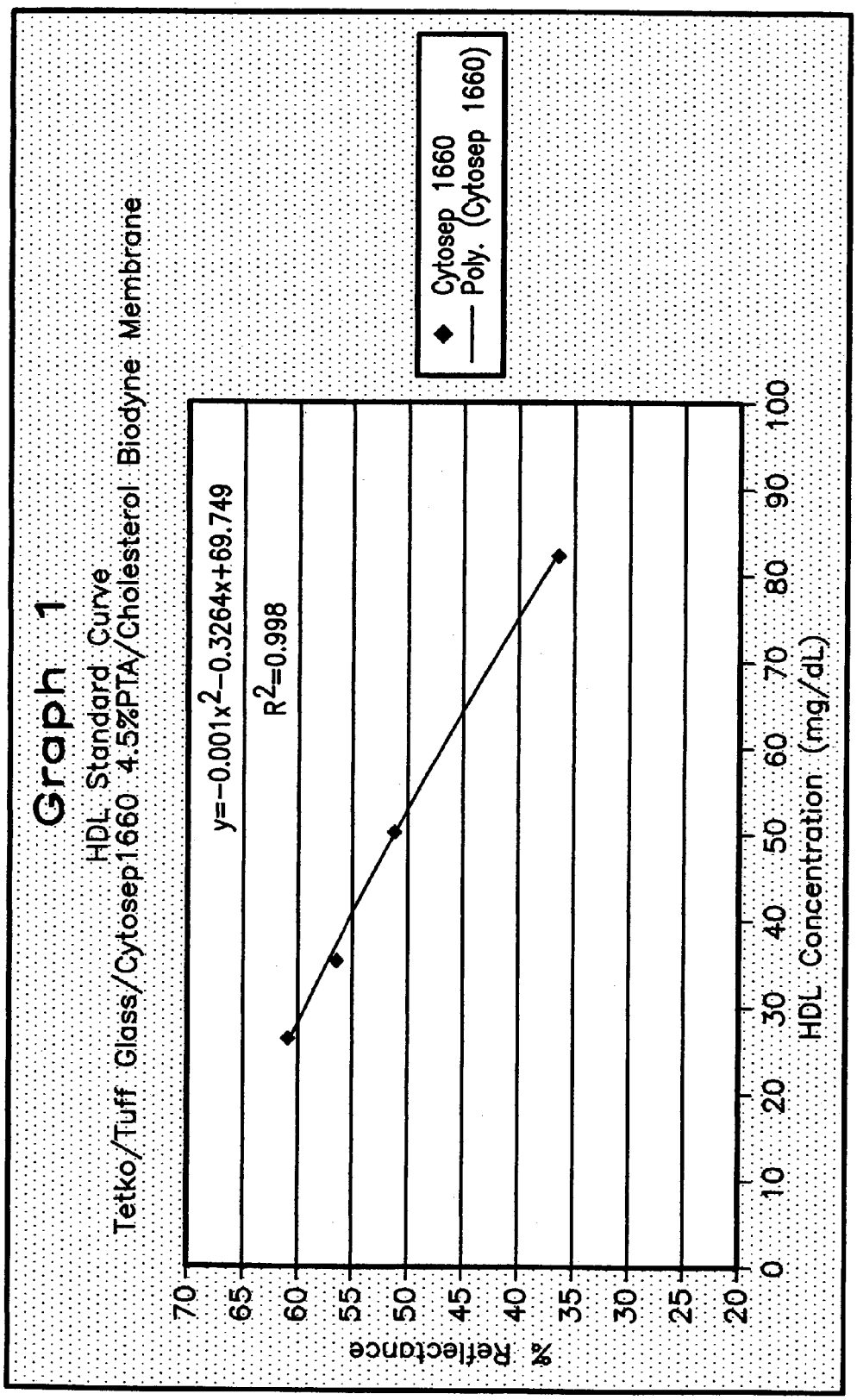
FIG. 4 is a graph of known HDL concentration versus measured reflectance for a test strip in accordance with example 8 of this disclosure.

In this example, a complete test apparatus 20 was used to measure the concentration of HDL and compare it with the known concentration. The blood separation layer 38 was prepared in accordance with Example 2. The HDL fractionation membrane 40 was a CytoSep® Grade 1660 of Examples 4–6 impregnated with a 4.5% Phosphotungstic Acid (PTA) solution of Example 6. The test strips were assembled in accordance with example 7. Fresh EDTA whole blood with various levels of HDL cholesterol were obtained and applied to the test strips. Percent reflectance using a red LED was recorded at the reaction endpoint. Table 1, below, shows in the left hand column the known concentration of HDL as determined with a wet chemistry automated clinical analyzer assay employed in the lab. In the right hand column is the percentage reflectance as obtained by a BIOSCANNER (Polymer Technology Systems, Inc.) spectrophotometer. The calibration curve generated with the data from table 1 is shown in FIG. 4. The correlation coefficient $R^2$ obtained by linear regression analysis was 0.998, which supports excellent correlation between reflectance and HDL concentration.

TABLE 1

Cytosep ® 1660 4.5% PTA

| HDL Concentration (mg/dL) | % Reflectance Mean (n = 10) |
|---|---|
| 26 | 60.91 |
| 35 | 56.40 |
| 50 | 51.21 |
| 82 | 35.99 |

EXAMPLE 9

Figure 5:
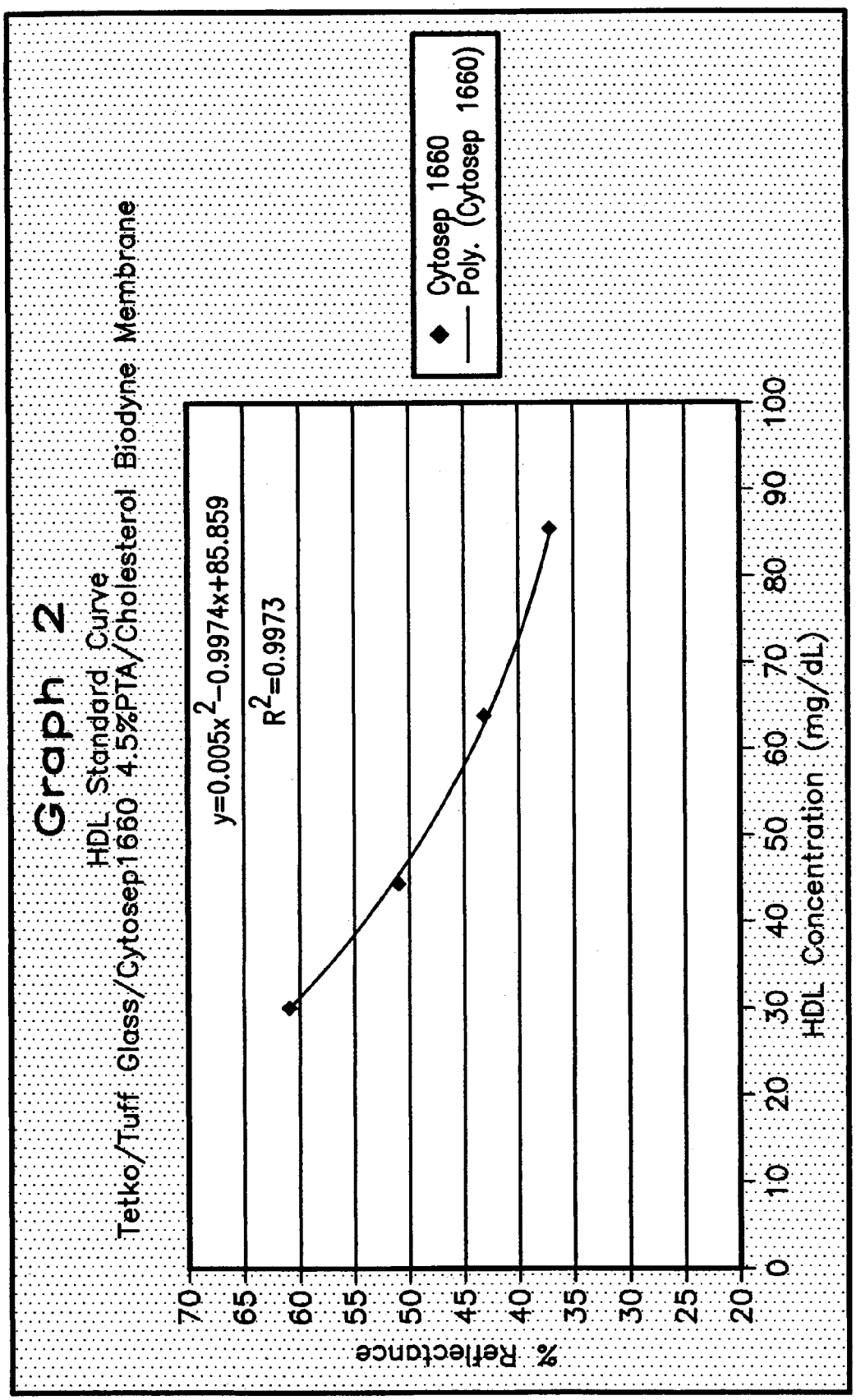
FIG. 5 is a graph of known HDL concentration versus measured reflectance for a test strip in accordance with example 9 of this disclosure.

The same tests as conducted in Example 8 were repeated with the results shown in table 2. The correlation between reflectance and known HDL concentration is depicted in graph 2 shown in FIG. 5. The calibration curve generated with the data from table 2 is shown in FIG. 5. The correlation coefficient $R^2$ obtained by linear regression analysis was 0.997, which supports excellent correlation between reflectance and HDL concentration.

TABLE 2

Cytosep ® 1660 4.5% PTA

| HDL Concentration (mg/dL) | % Reflectance Mean (n = 5) |
|---|---|
| 29 | 61.43 |
| 44 | 51.01 |
| 63 | 43.49 |
| 85 | 37.17 |

EXAMPLE 10

Figure 6:
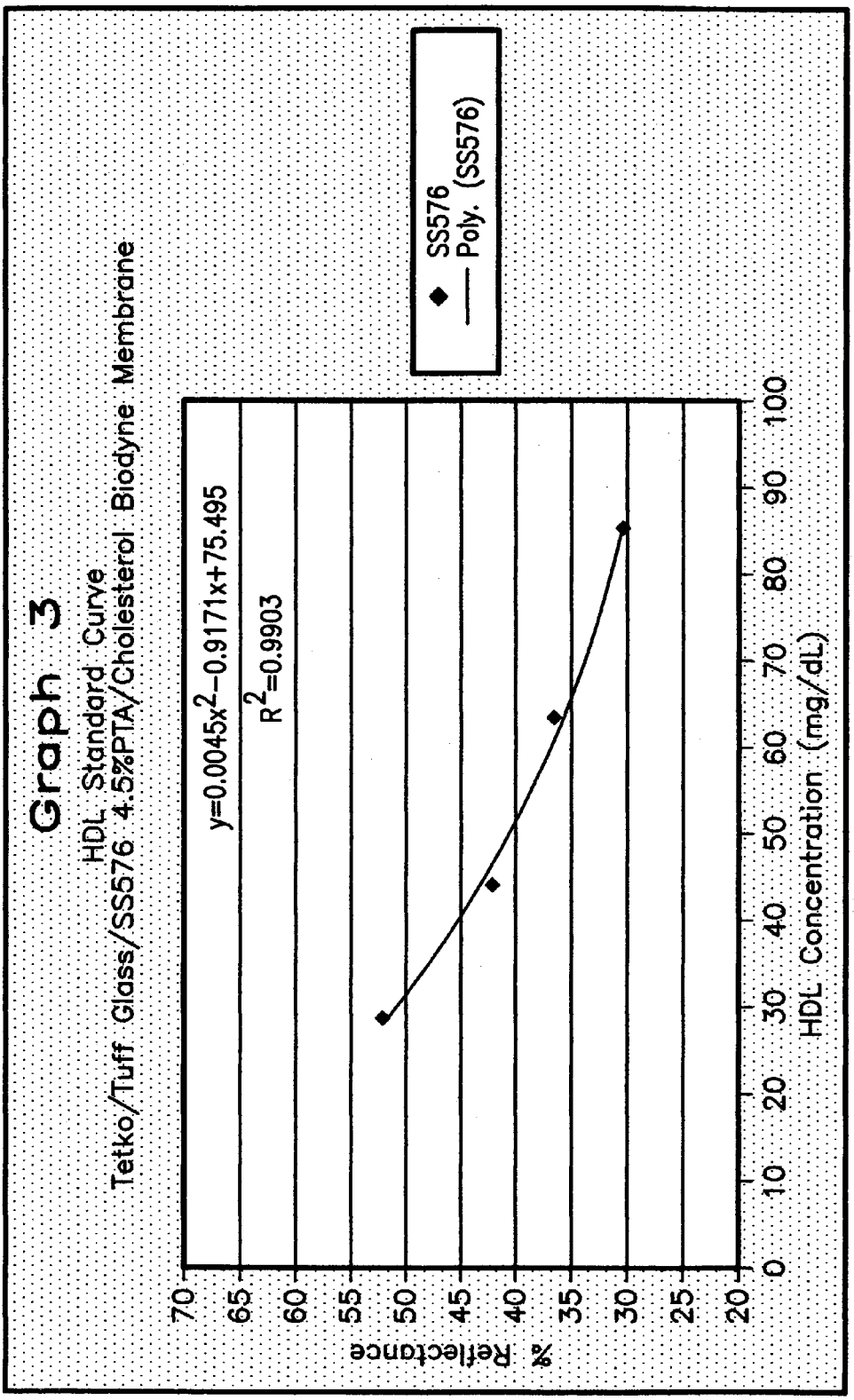
FIG. 6 is a graph of known HDL concentration versus measured reflectance for a test strip in accordance with example 10 of this disclosure.

Example 10 replaces the CytoSep® Grade 1660 membrane 40 with a Schleicher & Schull 576 membrane 40. All other test parameters were the same as in Example 8. Fresh EDTA whole blood with various levels of HDL Cholesterol were obtained and applied to the test strips. The results are shown in table 3. The calibration curve generated with the data from table 3 is shown in FIG. 6. The correlation coefficient $R^2$ obtained by linear regression analysis was 0.990, which supports excellent correlation between reflectance and HDL concentration.

TABLE 3

SS576, 4.5% PTA

| HDL Concentration (mg/dL) | % Reflectance Mean (n = 5) |
|---|---|
| 29 | 53.17 |
| 44 | 42.58 |
| 63 | 36.51 |
| 85 | 29.62 |

EXAMPLE 11

Figure 7:
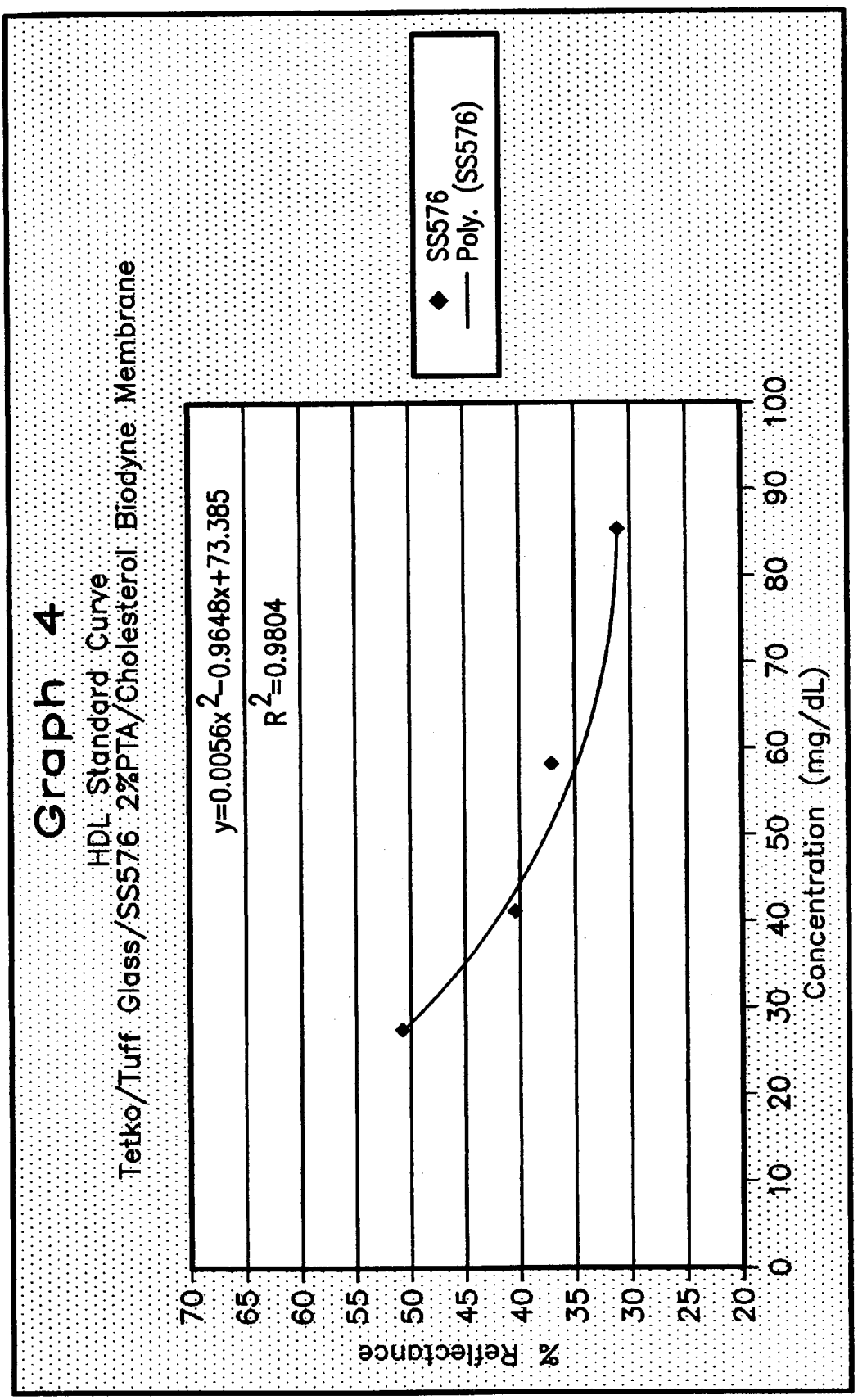
FIG. 7 is a graph of known HDL concentration versus measured reflectance for a test strip in accordance with example 11 of this disclosure.

Example 11 uses a Schleicher & Schull 576 membrane 40 and the impregnating solution of Example 5. All other test parameters were the same as in Example 8. Fresh EDTA whole blood with various levels of HDL Cholesterol were obtained and applied to the test strips. Percent reflectance using a red LED was recorded at the reaction endpoint. The results are shown in table 4. The calibration curve generated with the data from table 4 is shown in FIG. 7. The correlation coefficient $R^2$ obtained by linear regression analysis was 0.980, which supports excellent correlation between reflectance and HDL concentration.

TABLE 4

SS576 2% PTA

| HDL Concentration (mg/dL) | % Reflectance Mean (n = 5) |
|---|---|
| 29 | 50.68 |
| 44 | 40.23 |
| 63 | 35.87 |
| 85 | 31.20 |

EXAMPLE 12

Figure 8:
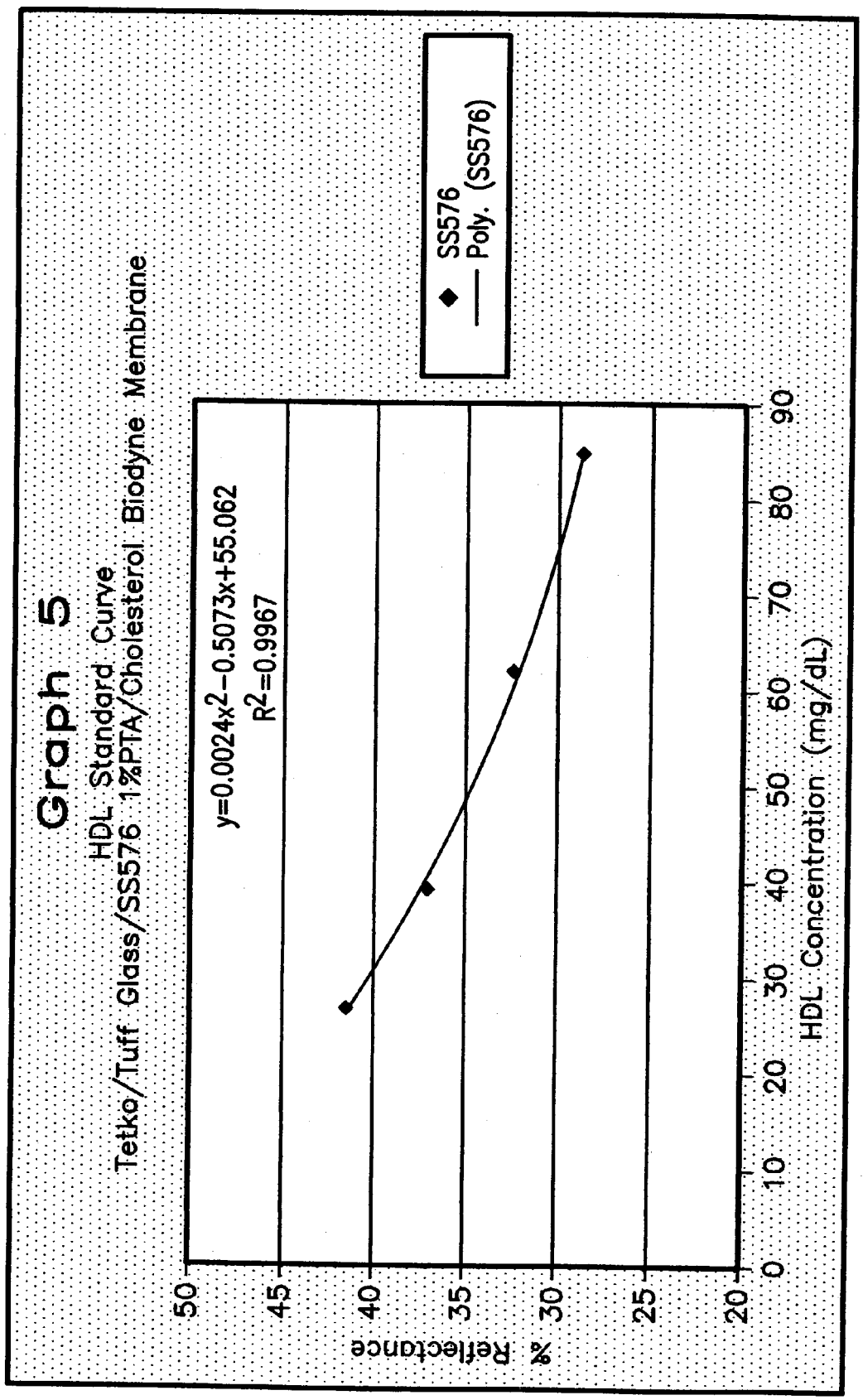
FIG. 8 is a graph of known HDL concentration versus measured reflectance for a test strip in accordance with example 12 of this disclosure.

Example 12 uses a Schleicher & Schull 576 membrane 40 and the impregnating solution of Example 4. All other test parameters were the same as in Example 8. Fresh EDTA whole blood with various levels of HDL Cholesterol were obtained and applied to the test strips. Percent reflectance using a red LED was recorded at the reaction endpoint. The results are shown in table 5. The calibration curve generated with the data from table 5 is shown in FIG. 8. The correlation coefficient $R^2$ obtained by linear regression analysis was 0.997, which supports excellent correlation between reflectance and HDL concentration.

TABLE 5

| HDL Concentration (mg/dL) | % Reflectance Mean (n = 5) |
|---|---|
| 29 | 42.54 |
| 44 | 36.98 |
| 63 | 32.98 |
| 85 | 29.21 |

EXAMPLE 13

Figure 9:
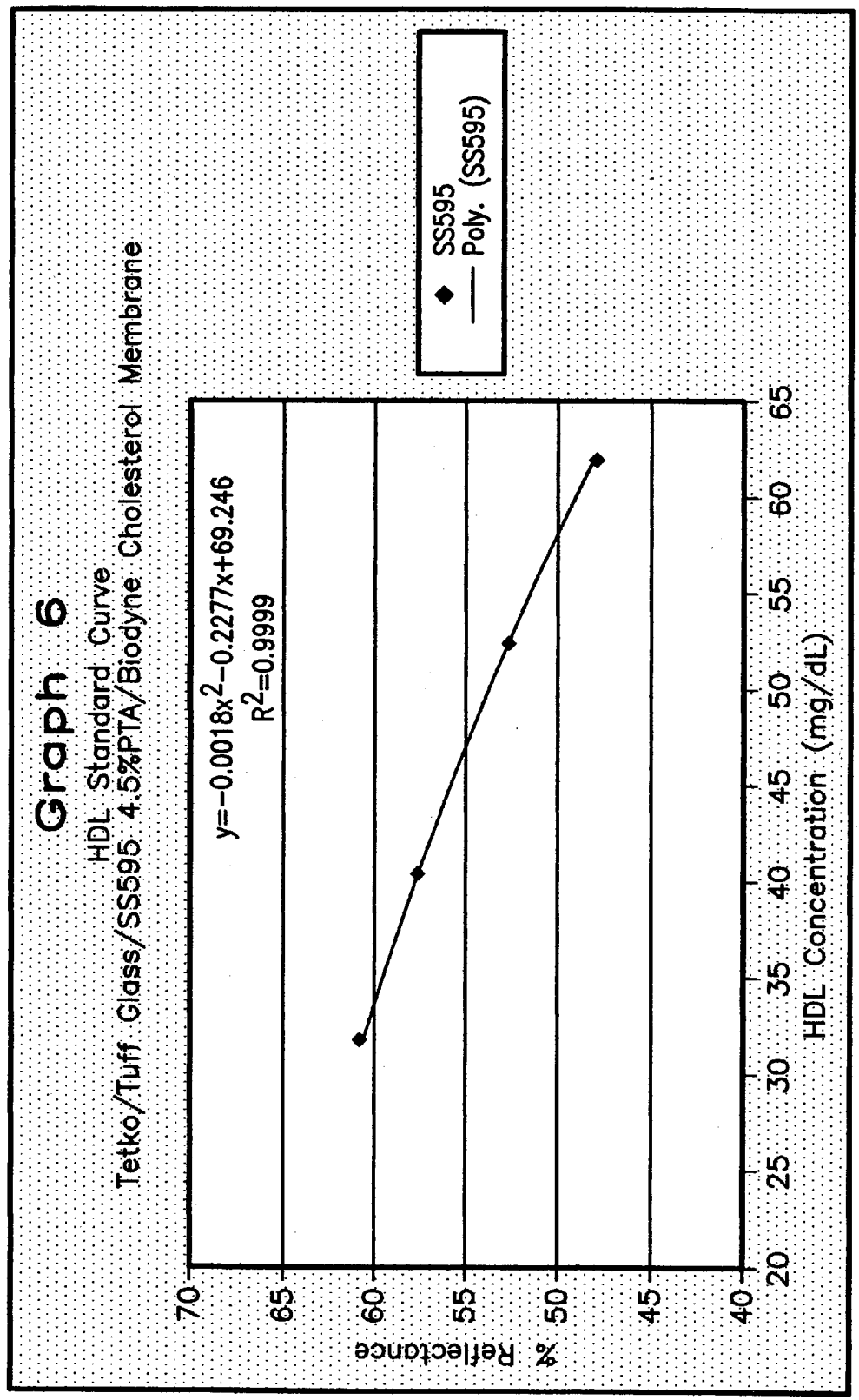
FIG. 9 is a graph of known HDL concentration versus measured reflectance for a test strip in accordance with example 13 of this disclosure.

Example 13 uses a Schleicher & Schull 595 membrane 40 and the impregnating solution of Example 6. All other test parameters were the same as in Example 8. Fresh EDTA whole blood with various levels of HDL Cholesterol were obtained and applied to the test strips. Percent reflectance using a red LED was recorded at the reaction endpoint. The results are shown in table 6. The calibration curve generated with the data from table 6 is shown in FIG. 9. The correlation coefficient $R^2$ obtained by linear regression analysis was 0.9999, which supports excellent correlation between reflectance and HDL concentration.

TABLE 6

SS595 4.5% PTA

| HDL Concentration (mg/dL) | % Reflectance Mean (n = 5) |
|---|---|
| 31 | 60.43 |
| 40 | 57.32 |
| 52 | 52.47 |
| 62 | 48.23 |

EXAMPLE 14

Figure 10:
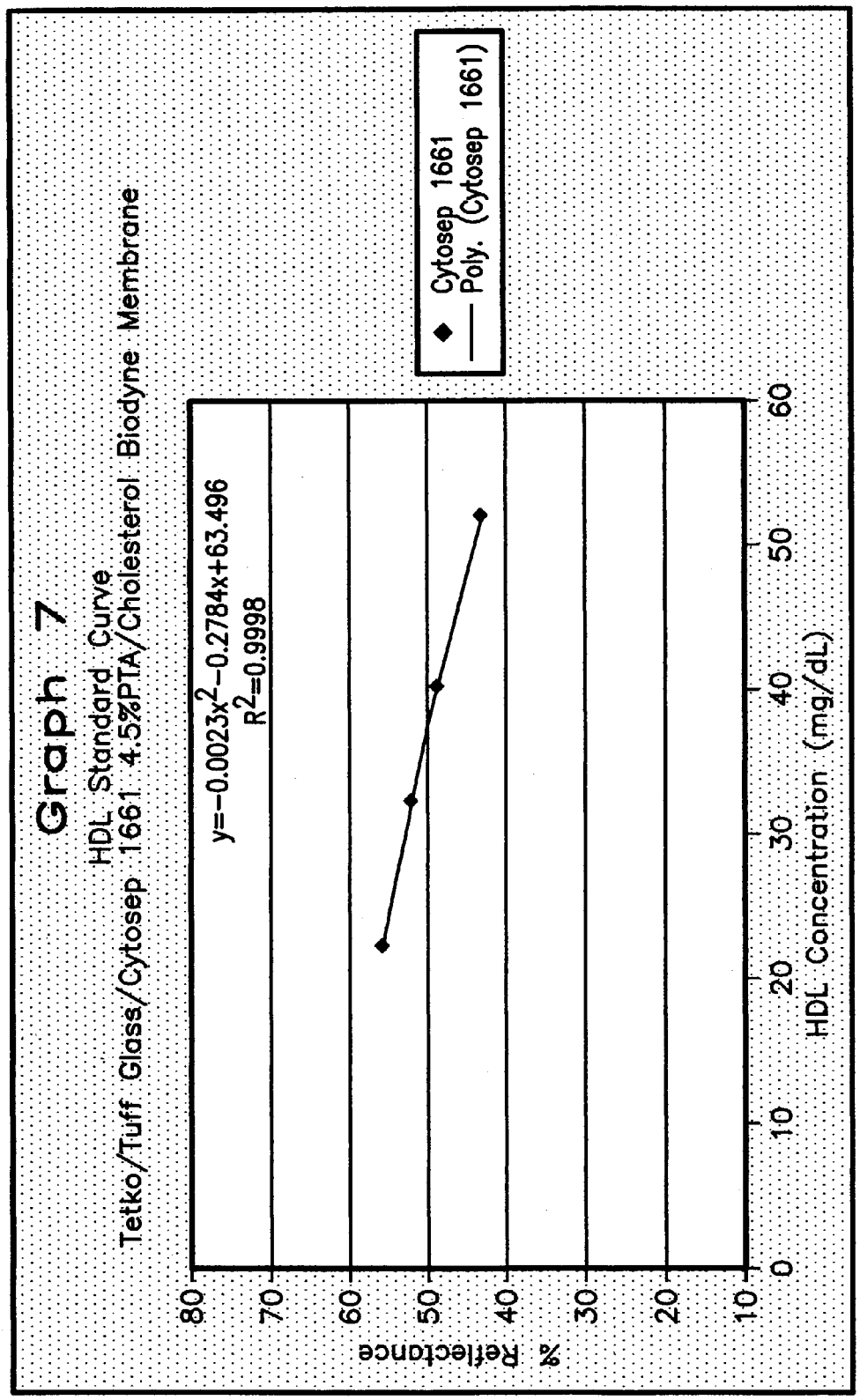
FIG. 10 is a graph of known HDL concentration versus measured reflectance for a test strip in accordance with example 14 of this disclosure.
Figure 11:
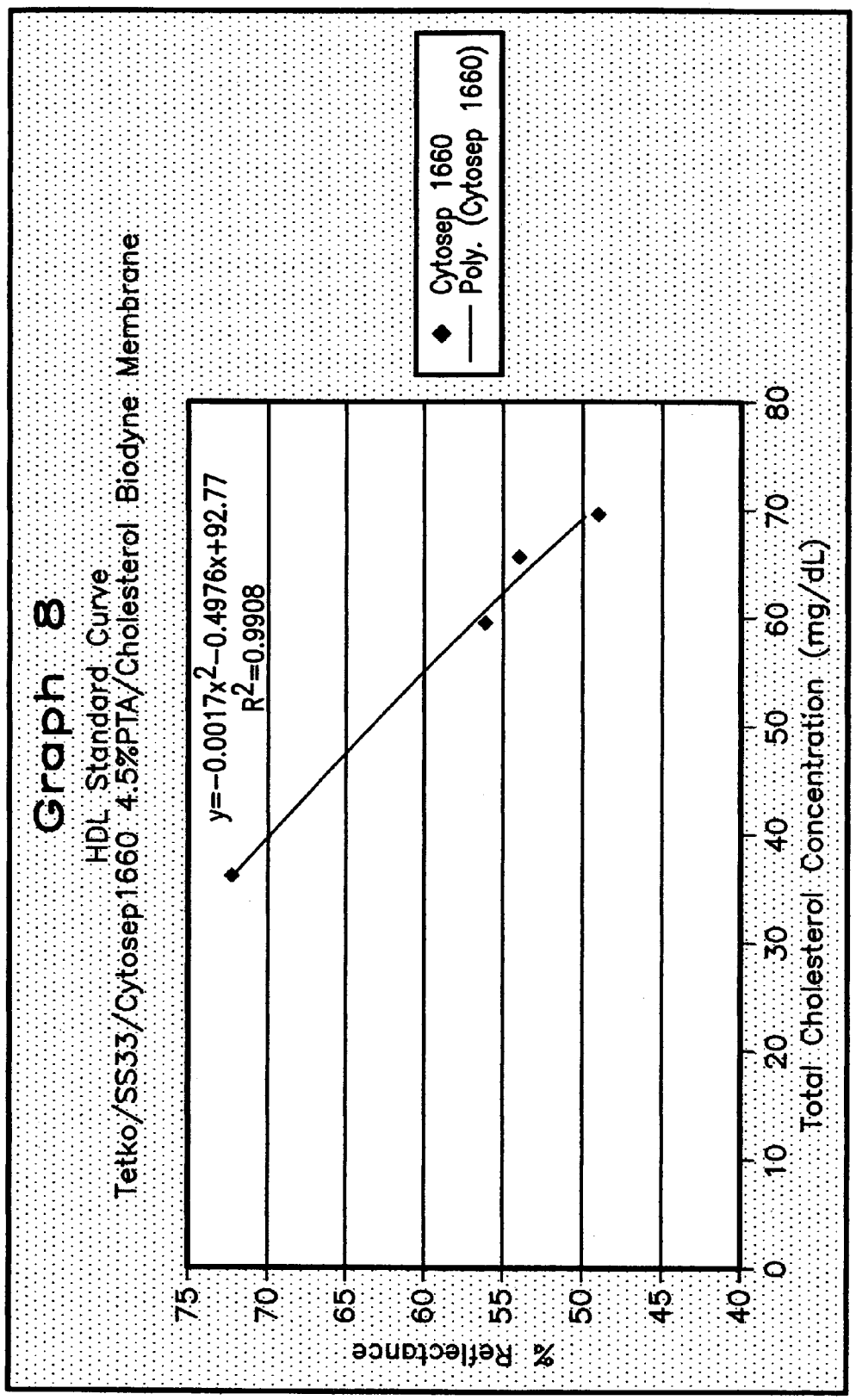
FIG. 11 is a graph of known HDL concentration versus measured reflectance for a test strip in accordance with example 15 of this disclosure.
Figure 12:
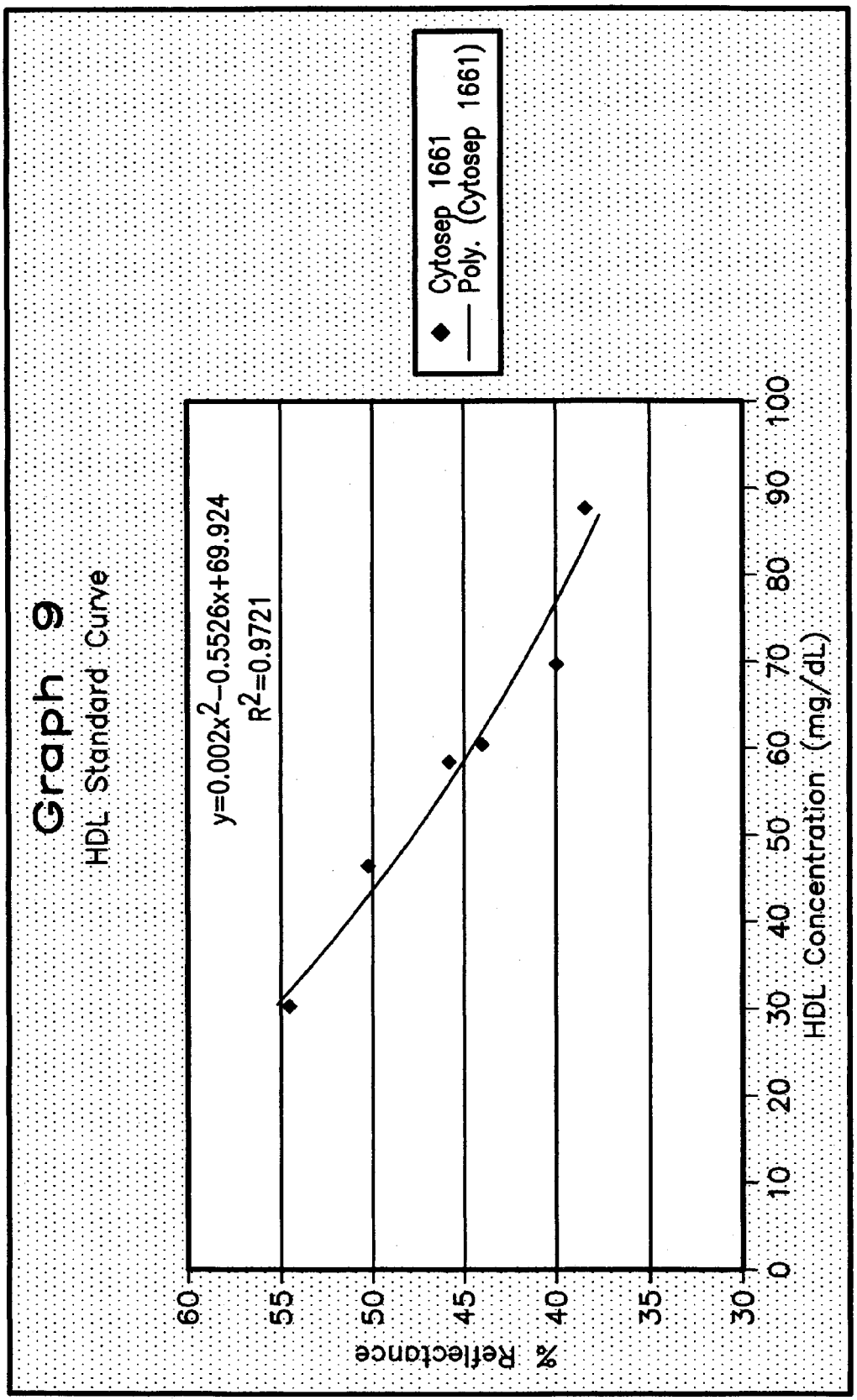
FIG. 12 is a graph of known HDL concentration versus measured reflectance for a test strip in accordance with example 16 of this disclosure.
Figure 13:
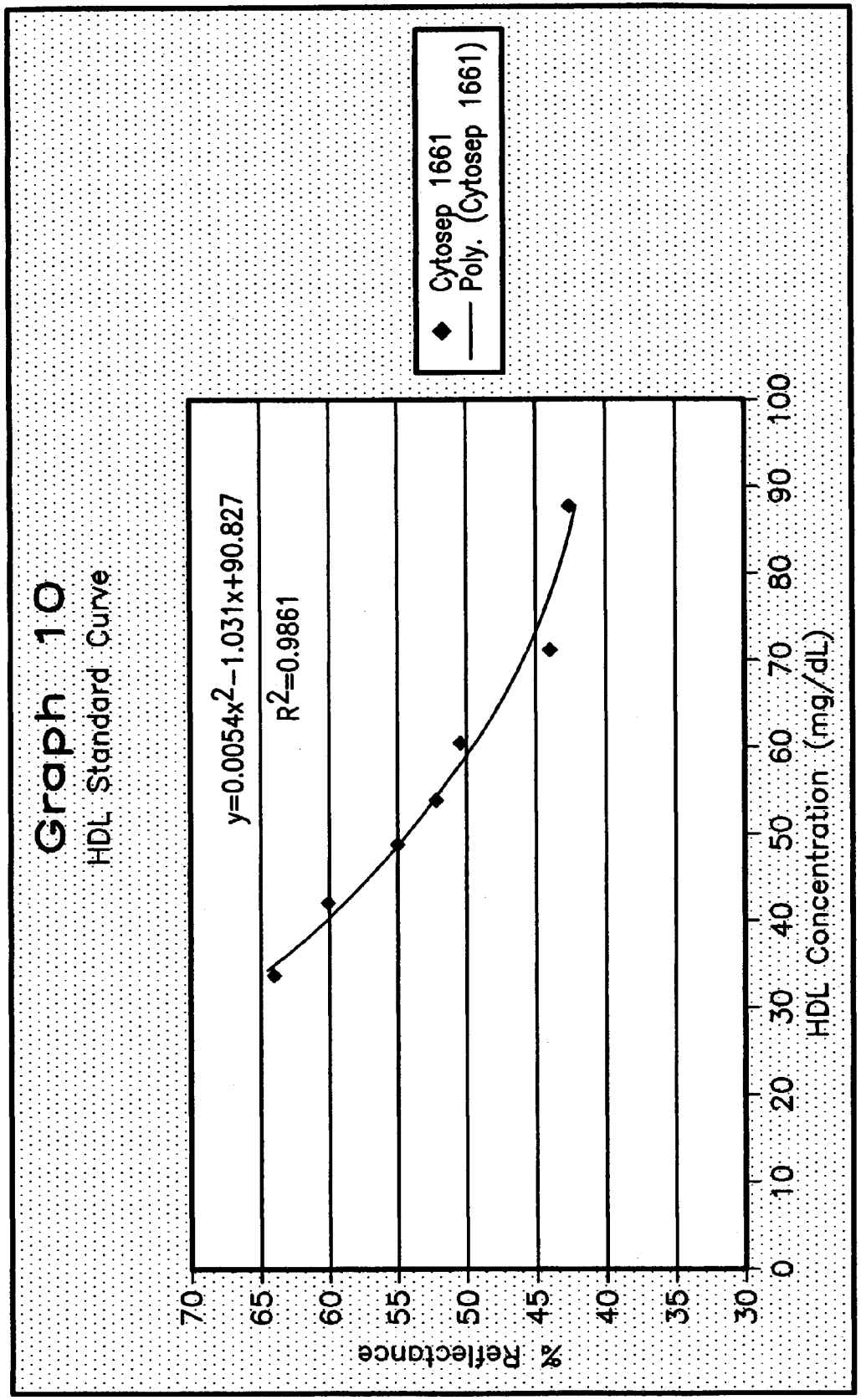
FIG. 13 is a graph of known HDL concentration versus measured reflectance for a test strip in accordance with example 17 of this disclosure.
Figure 14:
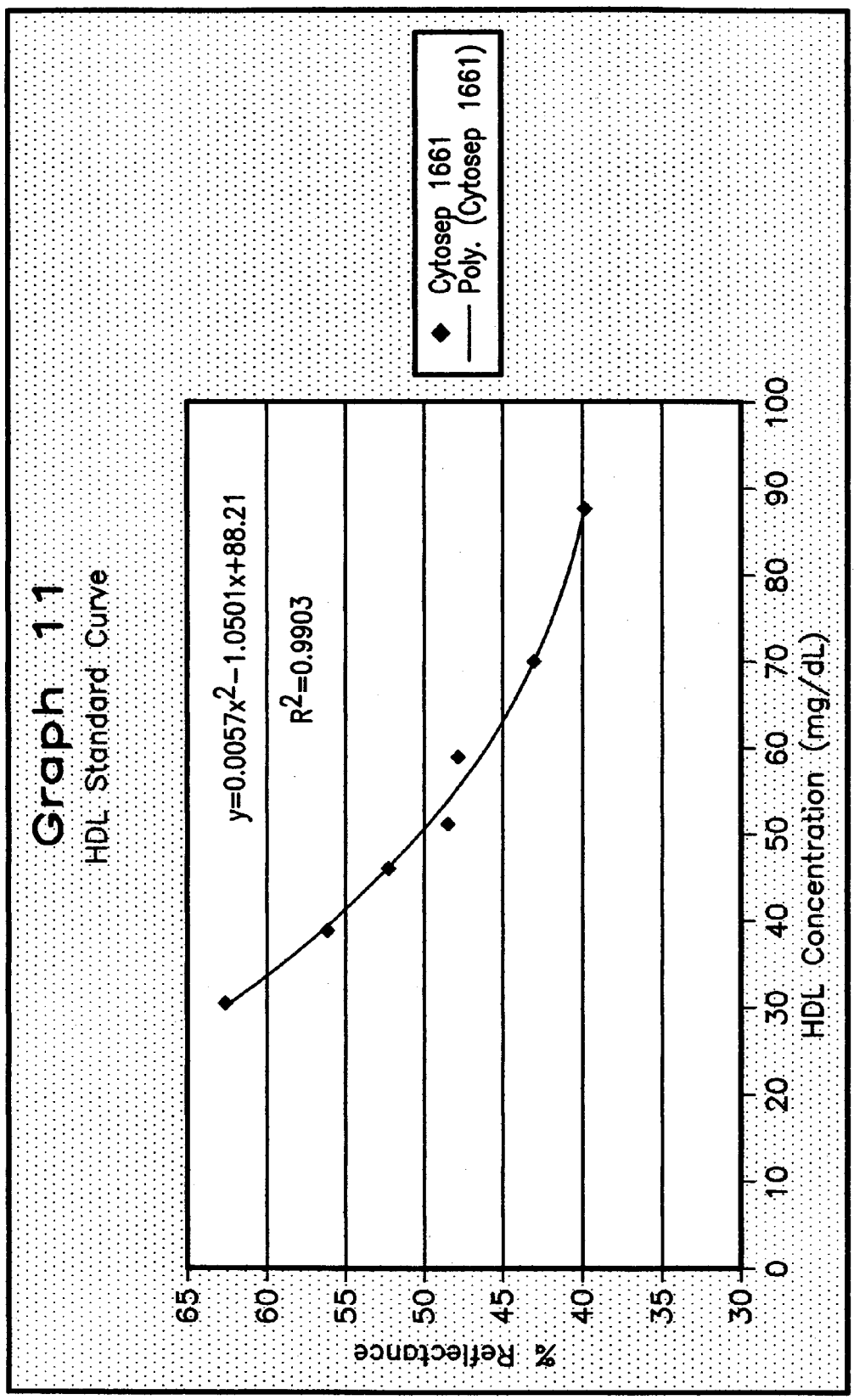
FIG. 14 is a graph of known HDL concentration versus measured reflectance for a test strip in accordance with example 18 of this disclosure.
Figure 15:
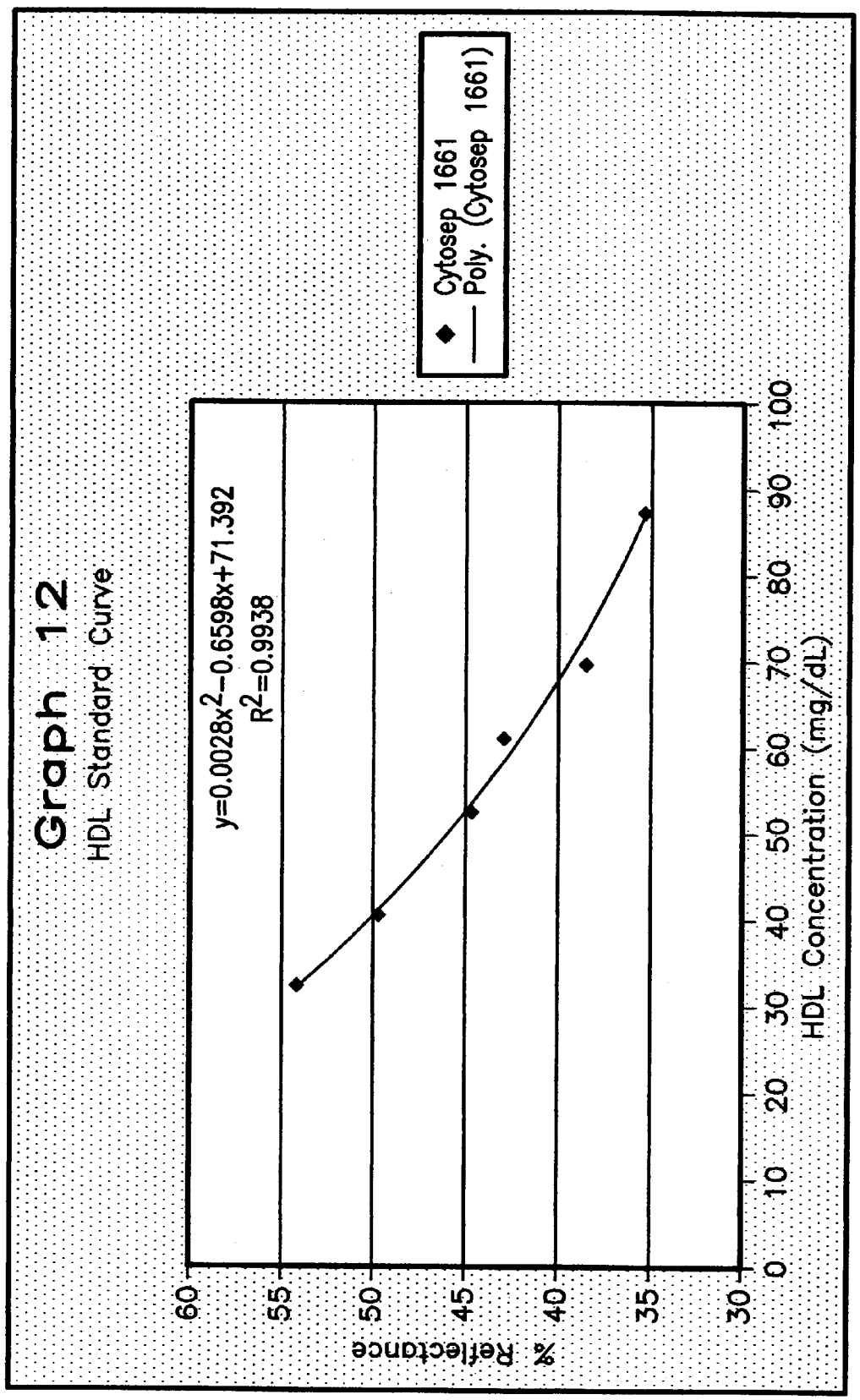
FIG. 15 is a graph of known HDL concentration versus measured reflectance for a test strip in accordance with example 19 of this disclosure.
Figure 16:
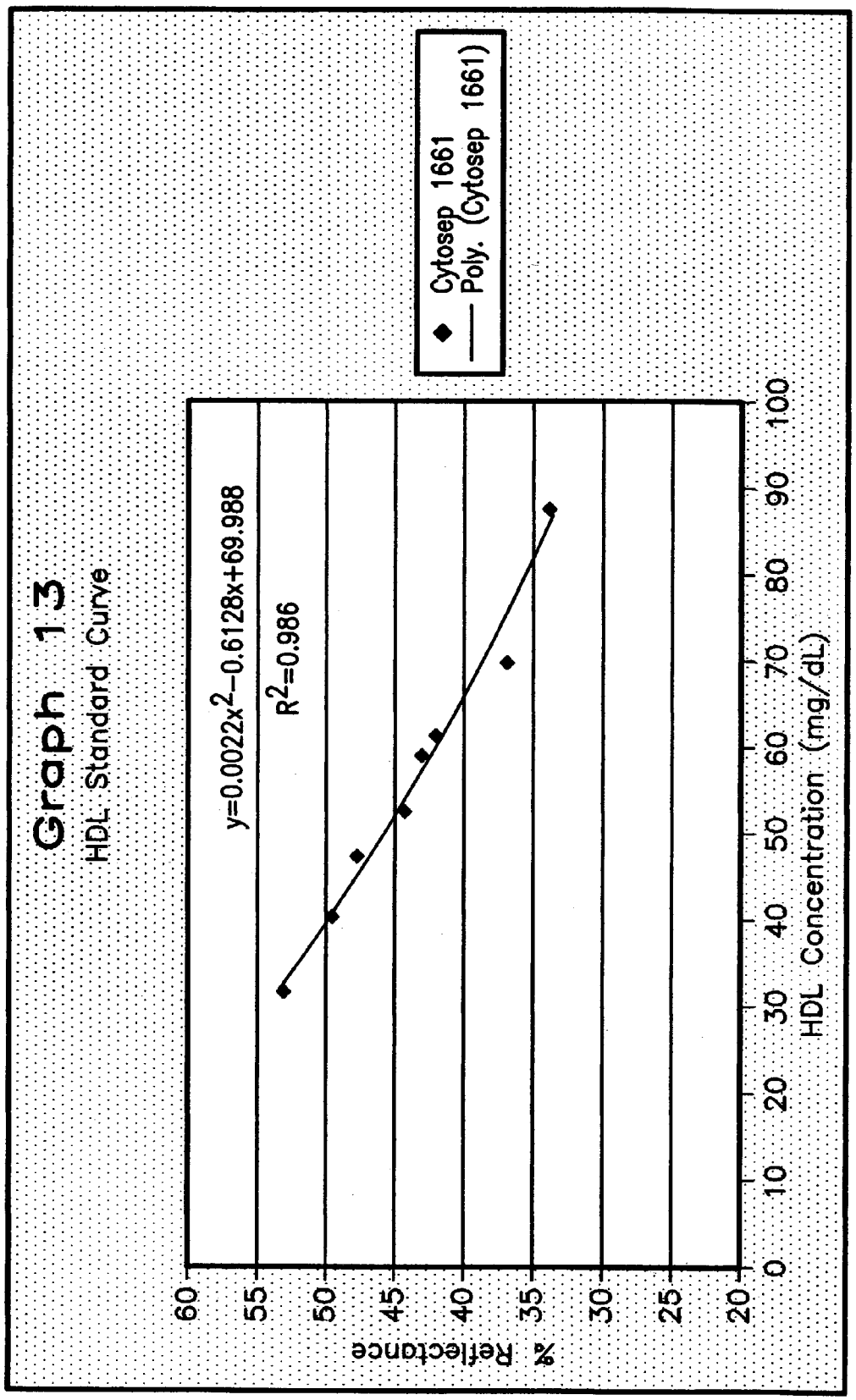
FIG. 16 is a graph of known HDL concentration versus measured reflectance for a test strip in accordance with example 20 of this disclosure.
Figure 17:
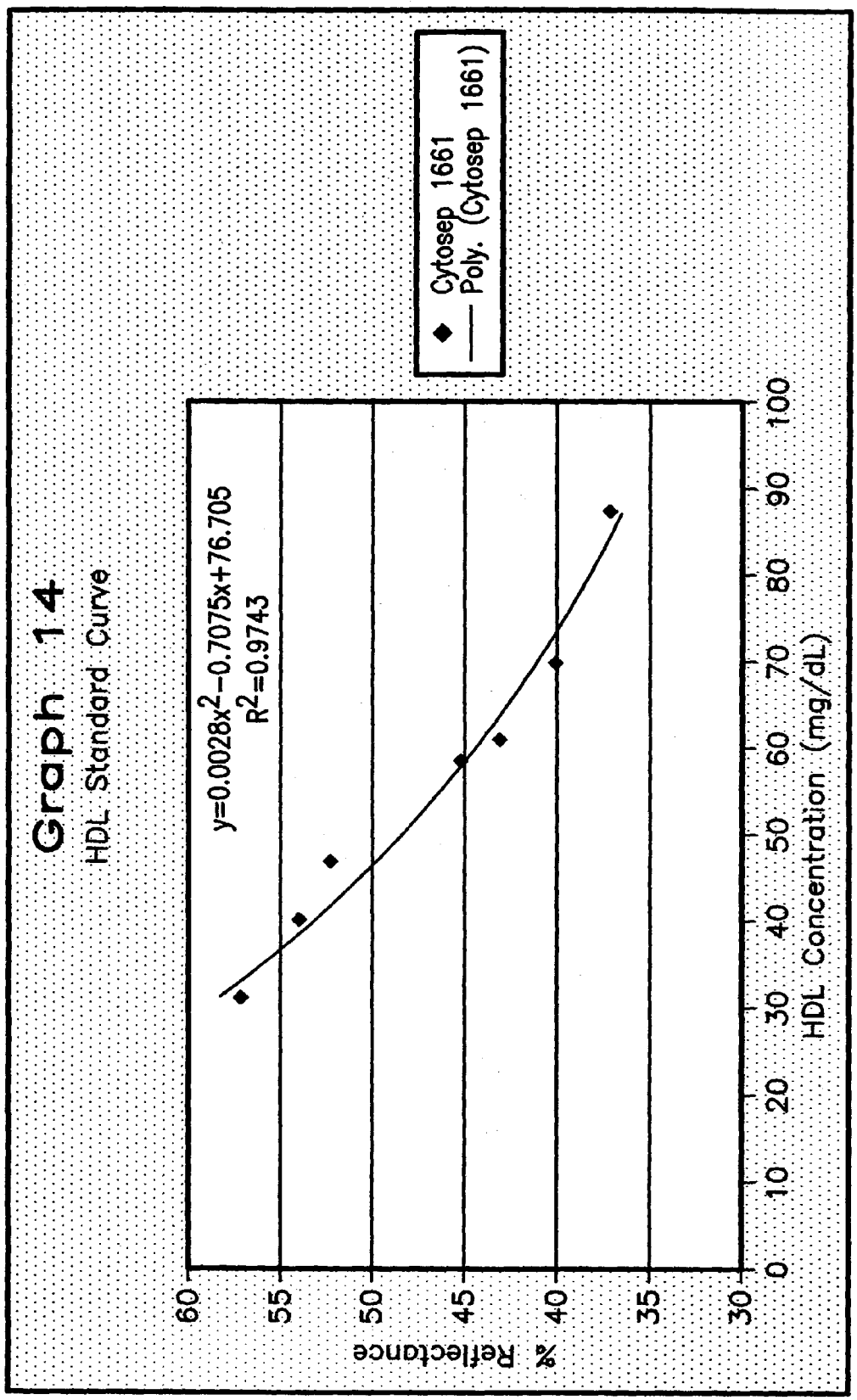
FIG. 17 is a graph of known HDL concentration versus measured reflectance for a test strip in accordance with example 21 of this disclosure.
Figure 18:
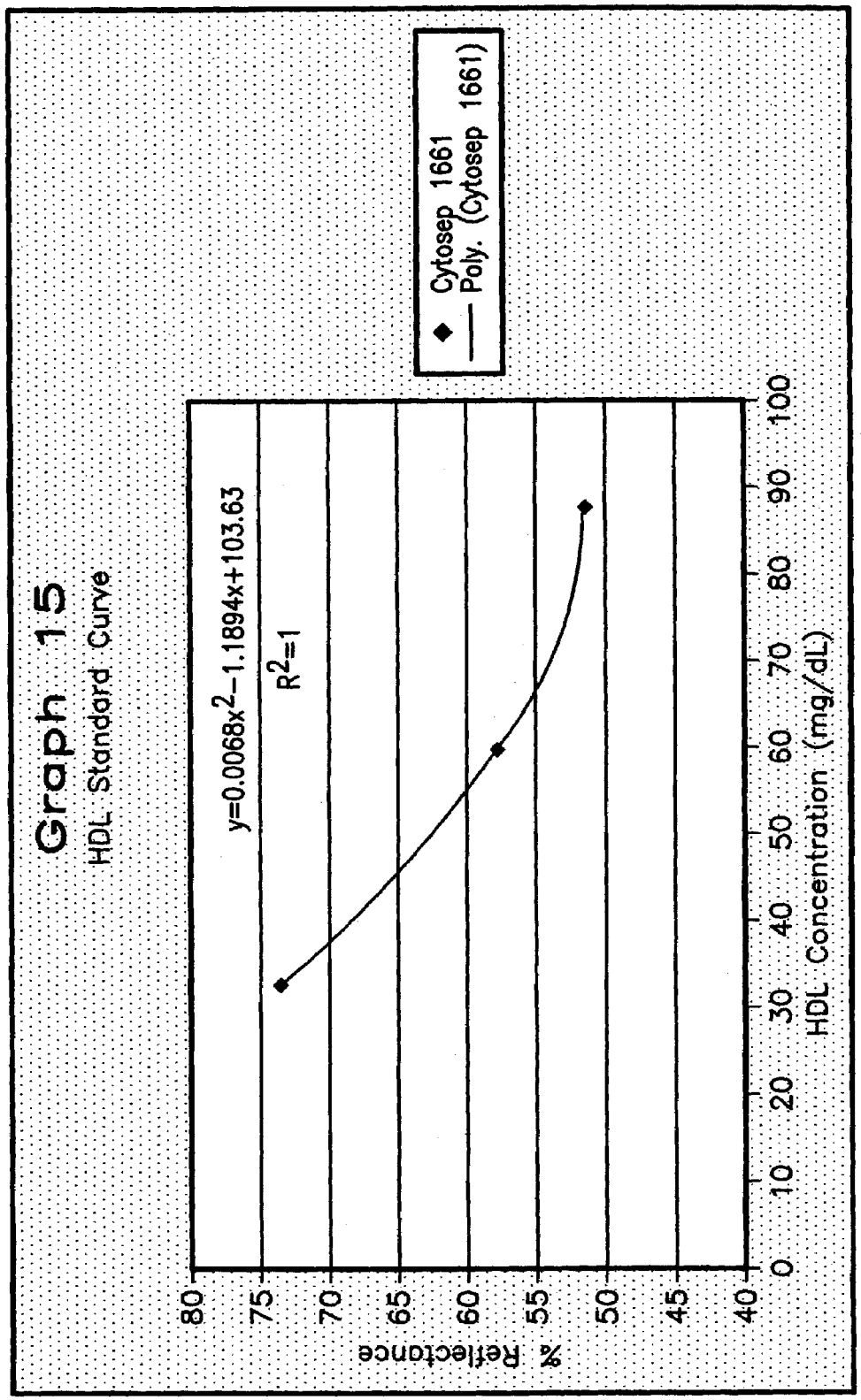
FIG. 18 is a graph of known HDL concentration versus measured reflectance for a test strip in accordance with example 22 of this disclosure.
Figure 19:
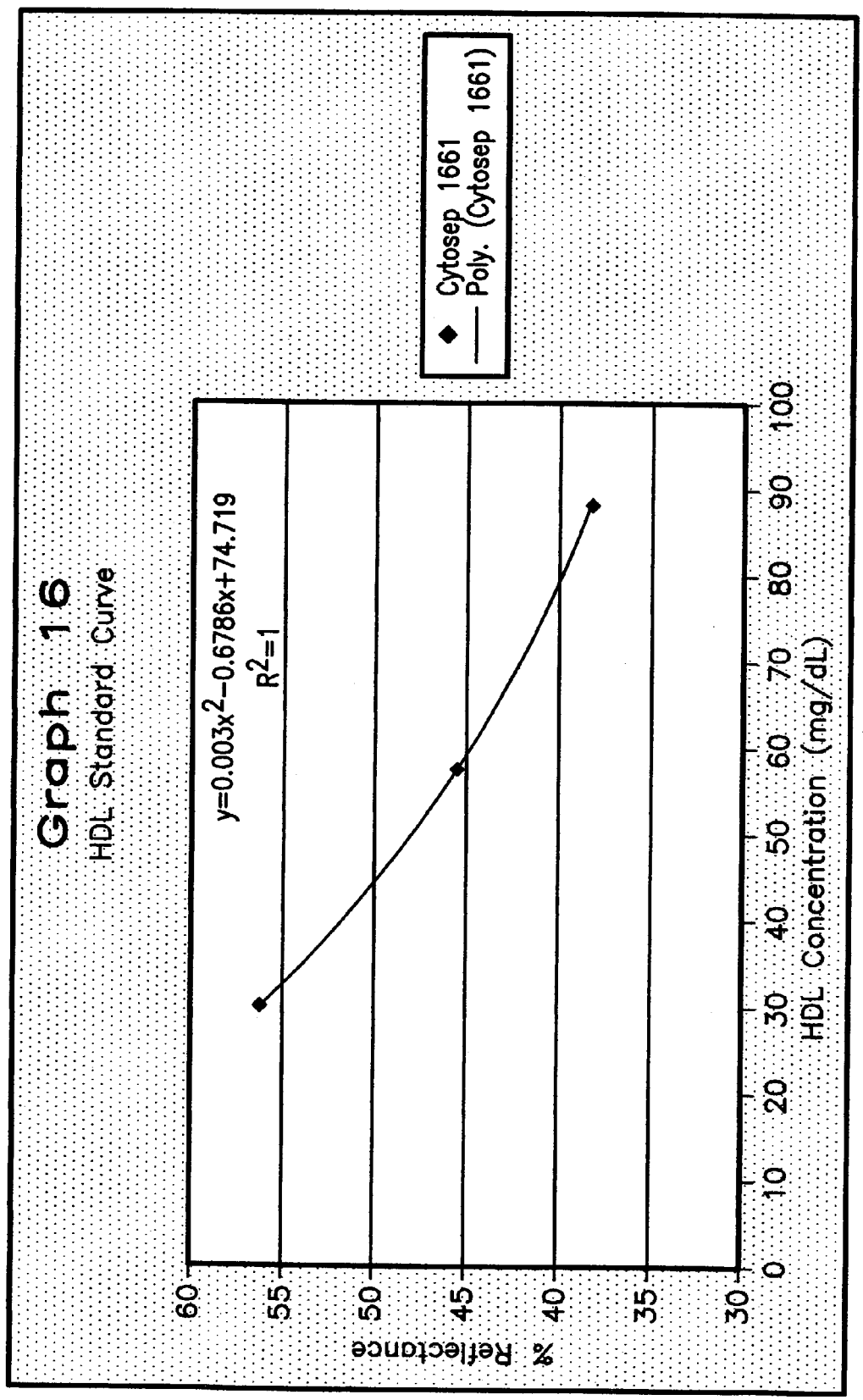
FIG. 19 is a graph of known HDL concentration versus measured reflectance for a test strip in accordance with example 23 of this disclosure.
Figure 20:
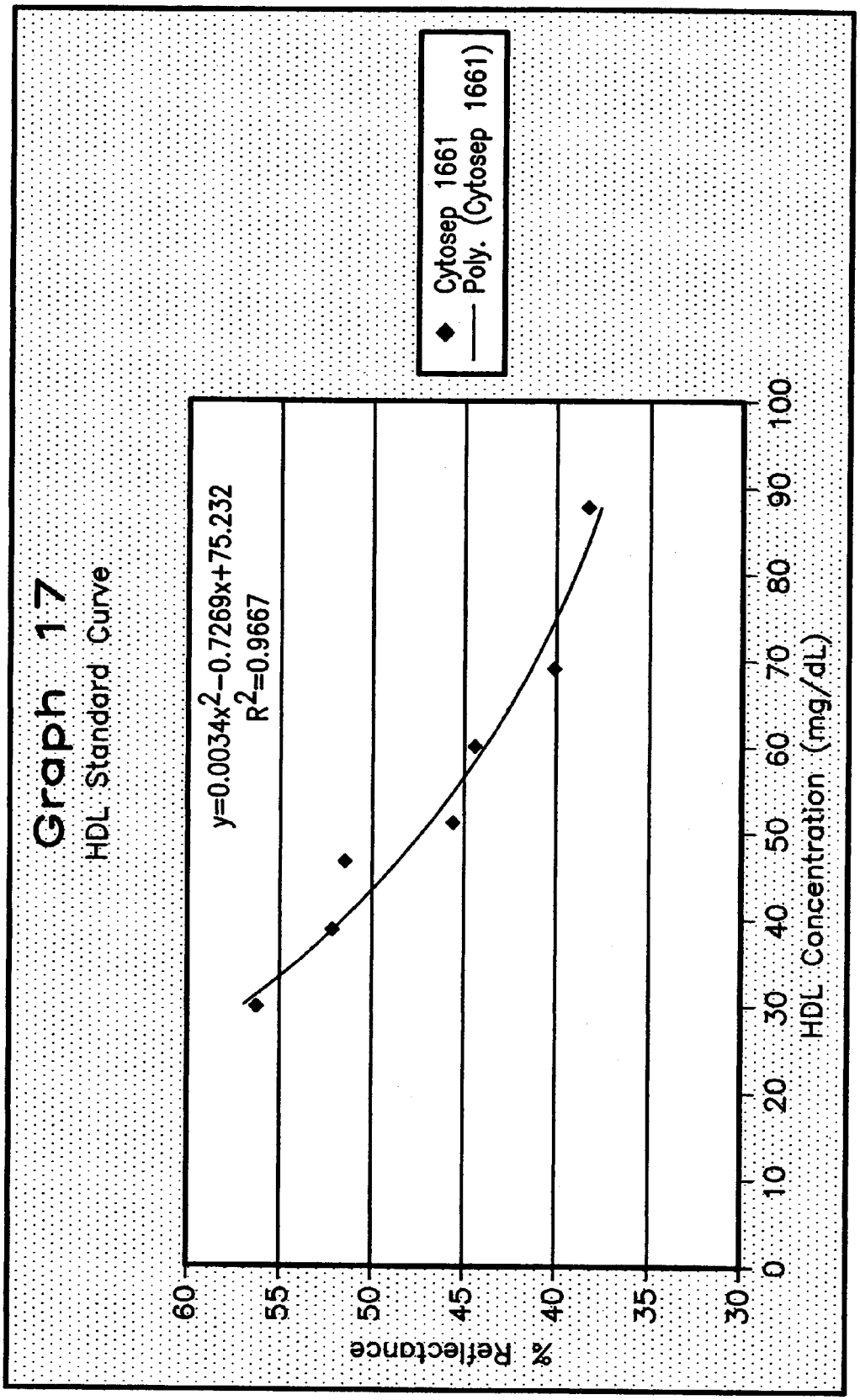
FIG. 20 is a graph of known HDL concentration versus measured reflectance for a test strip in accordance with example 24 of this disclosure.

Example 14 uses a CytoSep® Grade 1661 membrane 40 and the impregnating solution of Example 6. All other test parameters were the same as in Example 8. Fresh EDTA whole blood with various levels of HDL Cholesterol were obtained and applied to the test strips. Percent reflectance using a red LED was recorded at the reaction endpoint. The results are shown in table 7. The calibration curve generated with the data from table 7 is shown in FIG. 10. The correlation coefficient $R^2$ obtained by linear regression analysis was 0.9998, which supports excellent correlation between reflectance and HDL concentration.

TABLE 7

CytoSep 1661 4.5% PTA

| HDL Concentration (mg/dL) | % Reflectance Mean (n = 10) |
|---|---|
| 22 | 54.31 |
| 32 | 47.83 |
| 40 | 46.20 |

EXAMPLE 15

HDL Precipitation Using CytoSep Grade 1660 Impregnated with 4.5% Phosphotungstic Acid.

Test strips were assembled using membranes 38 prepared using the procedures analogous to Example 2 using Schleicher and Schuell Grade 33, which is a borosilicate glass fiber with acrylic latex binder (basis weight $g/m^2$=64, thickness µm=370, water absorbancy $g/100\ cm^2$=4.1) as blood separation membrane, Examples 3 and 6 and then assembled as in procedure analogous to Example 7. Fresh EDTA whole blood with various levels of HDL Cholesterol were obtained and applied to the test strips. Percent reflectance using a red LED was recorded at the reaction endpoint. Table 8 contains the data for Graph 8:

TABLE 8

Cytosep 1660 4.5% PTA

| HDL Concentration (mg/dL) | % Reflectance Mean (n = 10) |
|---|---|
| 36 | 72.69 |
| 60 | 56.09 |
| 66 | 53.90 |
| 70 | 48.86 |

EXAMPLE 16

HDL Precipitation Using CytoSep Grade 1661 Impregnated with 4.5% Phosphotungstic Acid.

Test strips were assembled using membranes 38 prepared using the procedures analogous to Example 2 using Whatman GF/DVA, which is a PVA bound glass fiber (basis weight $g/m^2$=120, thickness µm @ 53 kPa=780, standard porosity $s/100\ mL/in^2$=1.5, water absorption $mg/cm^2$=92) as blood separation membrane, Examples 3 and 6. Fresh EDTA whole blood with various levels of HDL Cholesterol were obtained and applied to the test strips. Percent reflectance using a red LED was recorded at the reaction endpoint. Table 9 contains the data for Graph 9:

TABLE 9

Cytosep 1661 4.5% PTA

| HDL Concentration (mg/dL) | % Reflectance Mean (n = 3) |
|---|---|
| 30 | 54.53 |
| 46 | 50.18 |
| 58 | 45.33 |
| 60 | 43.48 |
| 69 | 39.95 |
| 87 | 37.68 |

EXAMPLE 17

HDL Precipitation Using CytoSep Grade 1661 Impregnated with 4.5% Phosphotungstic Acid.

Test strips were assembled using membranes 38 prepared using the procedures analogous to Example 2 using Whatman GF/D, which is an unbound glass fiber (basis weight $g/m^2$=120, thickness µm @ 53 kPa=675, standard porosity $s/100\ mL/in^2$=2.3, water absorption $mg/cm^2$=102) as blood separation membrane, Examples 3 and 6. Fresh EDTA whole blood with various levels of HDL Cholesterol were obtained and applied to the test strips. Percent reflectance using a red LED was recorded at the reaction endpoint. Table 10 contains the data for Graph 10:

TABLE 10

Cytosep 1661 4.5% PTA

| HDL Concentration (mg/dL) | % Reflectance Mean (n = 3) |
|---|---|
| 30 | 64.06 |
| 39 | 59.86 |
| 46 | 54.72 |
| 51 | 52.08 |
| 58 | 50.26 |
| 69 | 43.91 |
| 87 | 42.49 |

EXAMPLE 18

HDL Precipitation Using CytoSep Grade 1661 Impregnated with 4.5% Phosphotungstic Acid.

Test strips were assembled using membranes 38 prepared using the procedures analogous to Example 2 using Whatman F145-02, which is a PVA bound glass fiber (basis weight g/m$^2$=120, thickness μm @ 53 kPa=785, standard porosity s/100 mL/in$^2$=1.9, water absorption mg/cm$^2$=88) as blood separation membrane, Examples 3 and 6. Fresh EDTA whole blood with various levels of HDL Cholesterol were obtained and applied to the test strips. Percent reflectance using a red LED was recorded at the reaction endpoint. Table 11 contains the data for Graph 11:

TABLE 11

Cytosep 1661 4.5% PTA

| HDL Concentration (mg/dL) | % Reflectance Mean (n = 3) |
|---|---|
| 30 | 62.16 |
| 39 | 55.63 |
| 46 | 51.91 |
| 51 | 48.16 |
| 58 | 47.66 |
| 69 | 42.79 |
| 87 | 39.64 |

EXAMPLE 19

HDL Precipitation Using CytoSep Grade 1661 Impregnated with 4.5% Phosphotungstic Acid.

Test strips were assembled using membranes 38 prepared using the procedures analogous to Example 2 using Whatman F147-11, which is a PVA bound glass fiber (basis weight g/m$^2$=60, thickness μm @ 53 kPa=370, standard porosity s/100 mL/in$^2$=3.7, water absorption mg/cm$^2$=42) as blood separation membrane, Examples 3 and 6. Fresh EDTA whole blood with various levels of HDL Cholesterol were obtained and applied to the test strips. Percent reflectance using a red LED was recorded at the reaction endpoint. Table 12 contains the data for Graph 12:

TABLE 12

Cytosep 1661 4.5% PTA

| HDL Concentration (mg/dL) | % Reflectance Mean (n = 3) |
|---|---|
| 30 | 54.23 |
| 39 | 49.73 |
| 51 | 44.69 |
| 60 | 42.85 |
| 69 | 38.55 |
| 87 | 35.26 |

EXAMPLE 20

HDL Precipitation Using CytoSep Grade 1661 Impregnated with 4.5% Phosphotungstic Acid.

Test strips were assembled using membranes 38 prepared using the procedures analogous to Example 2 using Whatman F487-14, which is a PVA bound glass fiber (basis weight g/m$^2$=45, thickness μm @ 53 kPa=235, standard porosity s/100 mL/in$^2$=5.3, water absorption mg/cm$^2$=25) as blood separation membrane, Examples 3 and 6. Fresh EDTA whole blood with various levels of HDL Cholesterol were obtained and applied to the test strips. Percent reflectance using a red LED was recorded at the reaction endpoint. Table 13 contains the data for Graph 13:

TABLE 13

Cytosep 1661 4.5% PTA

| HDL Concentration (mg/dL) | % Reflectance Mean (n = 3) |
|---|---|
| 30 | 53.07 |
| 39 | 49.62 |
| 46 | 47.24 |
| 51 | 43.90 |
| 58 | 42.34 |
| 60 | 41.38 |
| 69 | 36.55 |
| 87 | 33.56 |

EXAMPLE 21

HDL precipitation using CytoSep Grade 1661 impregnated with 4.5% Phosphotungstic Acid. Test strips were assembled using membranes 38 prepared using the procedures analogous to Example 2 using Whatman F487-09, which is an unbound glass fiber (basis weight g/m$^2$=45, thickness μm @ 53 kPa=220, standard porosity s/100 mL/in$^2$=5.3, water absorption mg/cm$^2$=30) as blood separation membrane, Examples 3 and 6. Fresh EDTA whole blood with various levels of HDL Cholesterol were obtained and applied to the test strips. Percent reflectance using a red LED was recorded at the reaction endpoint. Table 14 contains the data for Graph 14:

TABLE 14

| Cytosep 1661 4.5% PTA | |
|---|---|
| HDL Concentration (mg/dL) | % Reflectance Mean (n = 3) |
| 30 | 56.86 |
| 39 | 53.84 |
| 46 | 52.11 |
| 58 | 45.13 |
| 60 | 43.15 |
| 69 | 39.92 |
| 87 | 36.77 |

EXAMPLE 22

HDL precipitation using CytoSep Grade 1661 impregnated with 4.5% Phosphotungstic Acid. Test strips were assembled using membranes 38 prepared using the procedures analogous to Example 2 using Schleicher and Schuell Grade 30, which is a binderless borosilicate glass fiber (basis weight g/m$^2$=66, thickness µm=342) as blood separation membrane, Examples 3 and 6. Fresh EDTA whole blood with various levels of HDL Cholesterol were obtained and applied to the test strips. Percent reflectance using a red at the reaction endpoint. Table 15 contains the data for Graph 15:

TABLE 15

| Cytosep 1661 4.5% PTA | |
|---|---|
| HDL Concentration (mg/dL) | % Reflectance Mean (n = 3) |
| 30 | 74.03 |
| 58 | 57.37 |
| 87 | 51.28 |

EXAMPLE 23

HDL Precipitation Using CytoSep Grade 1661 Impregnated with 4.5% Phosphotungstic Acid.

Test strips were assembled using membranes 38 prepared using the procedures analogous to Example 2 using Schleicher and Schuell Grade 31, which is a binderless borosilicate glass fiber (basis weight g/m$^2$=53, thickness µm=270) as blood separation membrane, Examples 3 and 6. Fresh EDTA whole blood with various levels of HDL Cholesterol were obtained and applied to the test strips. Percent reflectance using a red LED was recorded at the reaction endpoint. Table 16 contains the data for Graph 16:

TABLE 16

| Cytosep 1661 4.5% PTA | |
|---|---|
| HDL Concentration (mg/dL) | % Reflectance Mean (n = 3) |
| 30 | 57.09 |
| 58 | 45.56 |
| 87 | 38.63 |

EXAMPLE 24

HDL Precipitation Using CytoSep Grade 1661 Impregnated with 4.5% Phosphotungstic Acid.

Test strips were assembled using membranes 38 prepared using the procedures analogous to Example 2 using Schleicher and Schuell Grade 33, which is a borosilicate glass fiber with acrylic latex binder (basis weight g/m$^2$=64, thickness µm=370, water absorbancy g/100 cm$^2$=4.1) as blood separation membrane, Examples 3 and 6. Fresh EDTA whole blood with various levels of HDL Cholesterol were obtained and applied to the test strips. Percent reflectance using a red LED was recorded at the reaction endpoint. Table 17 contains the data for Graph 17:

TABLE 17

| Cytosep 1661 4.5% PTA | |
|---|---|
| HDL Concentration (mg/dL) | % Reflectance Mean (n = 3) |
| 30 | 55.89 |
| 39 | 51.92 |
| 46 | 51.10 |
| 51 | 45.62 |
| 60 | 44.26 |
| 69 | 39.86 |
| 87 | 37.88 |

Mechanics of Fluid Movement in Strip 20

As noted above, the mechanism by which the inventive HDL strips of the present invention operate has become better understood since the filing of provisional patent application 60/342,790. To ascertain the nature of fluid movement and blood separation in strips 20, several strips were analyzed by applying a 15 microliter sample of whole blood, immersing the strip in liquid nitrogen to freeze the blood (and other fluids), then sectioning across the long axis of the strip using a microtome, then photographing through a microscope under cryogenic conditions to ensure that the fluids remained frozen. By using this technique, the sample can be allowed to react with the test strip for a specified period of time, then all further fluid flow and color development is halted while the strip is sectioned and photographed. The magnification of the microscope was 50×, and the film was digitized to provide digital images.

The digital images are schematically represented in FIGS. 21–24. Quite remarkably and surprisingly, fluid flow and blood separation take place much faster than the inventors had anticipated. With reference to FIG. 21, rim or cylindrical boss 44 presses against layer 36 and the stack and reaction layer 42 is abutting shelf 55. Due to the compression of layers 36–42 between boss 44 and shelf 55, the profile of the layers is not quite flat, but instead bulges slightly in the center of the aligned openings 32 and 34. As noted above, this compressive force helps speed fluid movement. Indeed, after only one second, the portion of fluid containing significant red blood cells is shown at 57 and has already moved through layer 36, most of the way through layer 38 and even partly into layer 40. This occurs before the blood application window 32 is emptied. The portion of fluid believed to be essentially clear plasma is shown at 59, and is believed to have penetrated significantly into layer 40, and possibly into reaction layer 42, even within one (1) second. This incredible speed of fluid movement within the layers of strip 20 is attributed to (1) selection of material for the layers and relative arrangement (e.g., open glass matrix 38 followed by more tightly packed, finer texture glass matrix 40 thereunder), (2) agents impregnating the various layers and (3) the compressive force with which the layers are held in strip 20.

Figure 22:
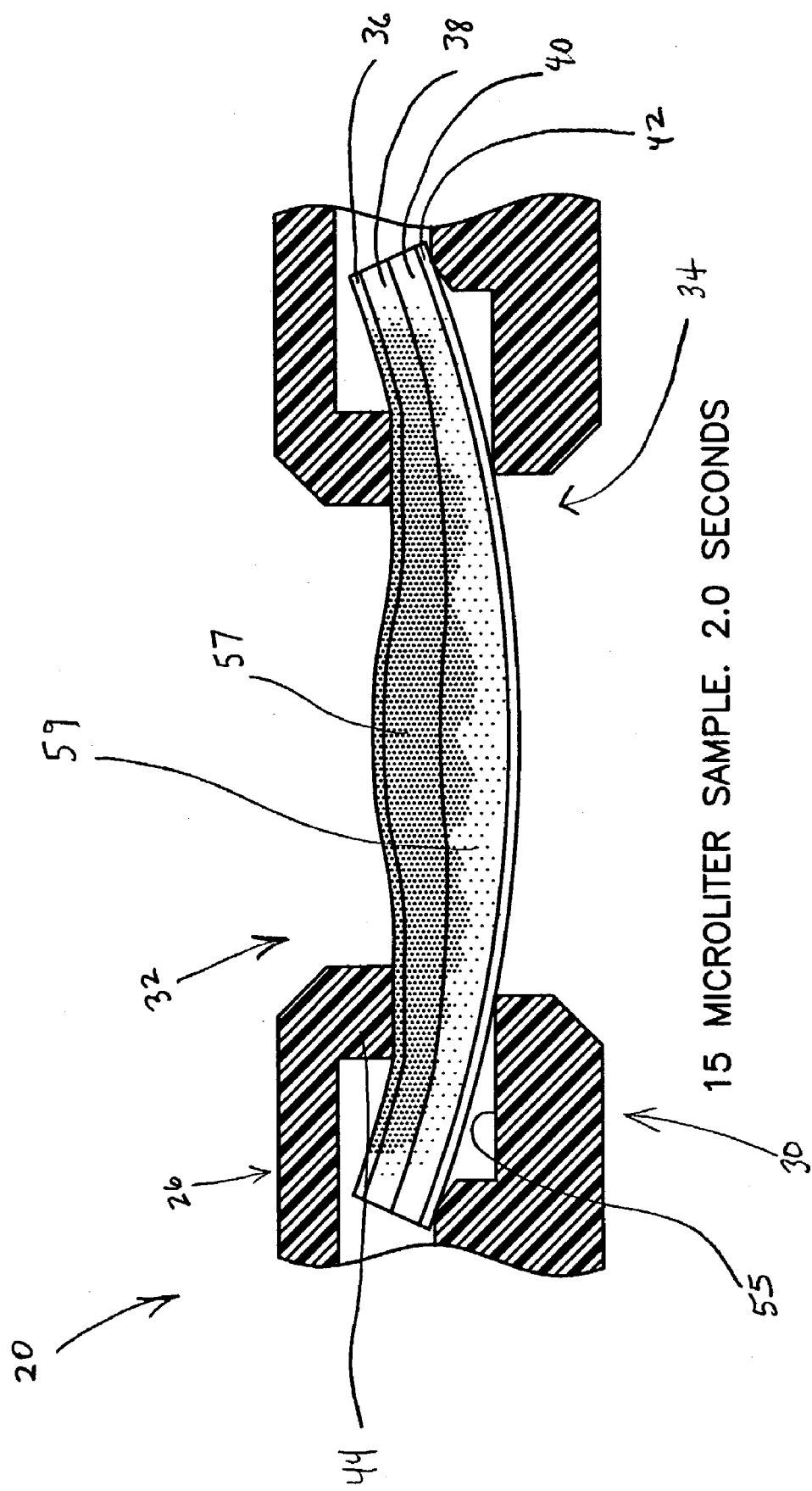
FIG. 22 is a cross sectional view of the test strip of FIG. 21 showing movement of blood and plasma at 2.0 seconds after the blood sample has been applied to the strip.
Figure 23:
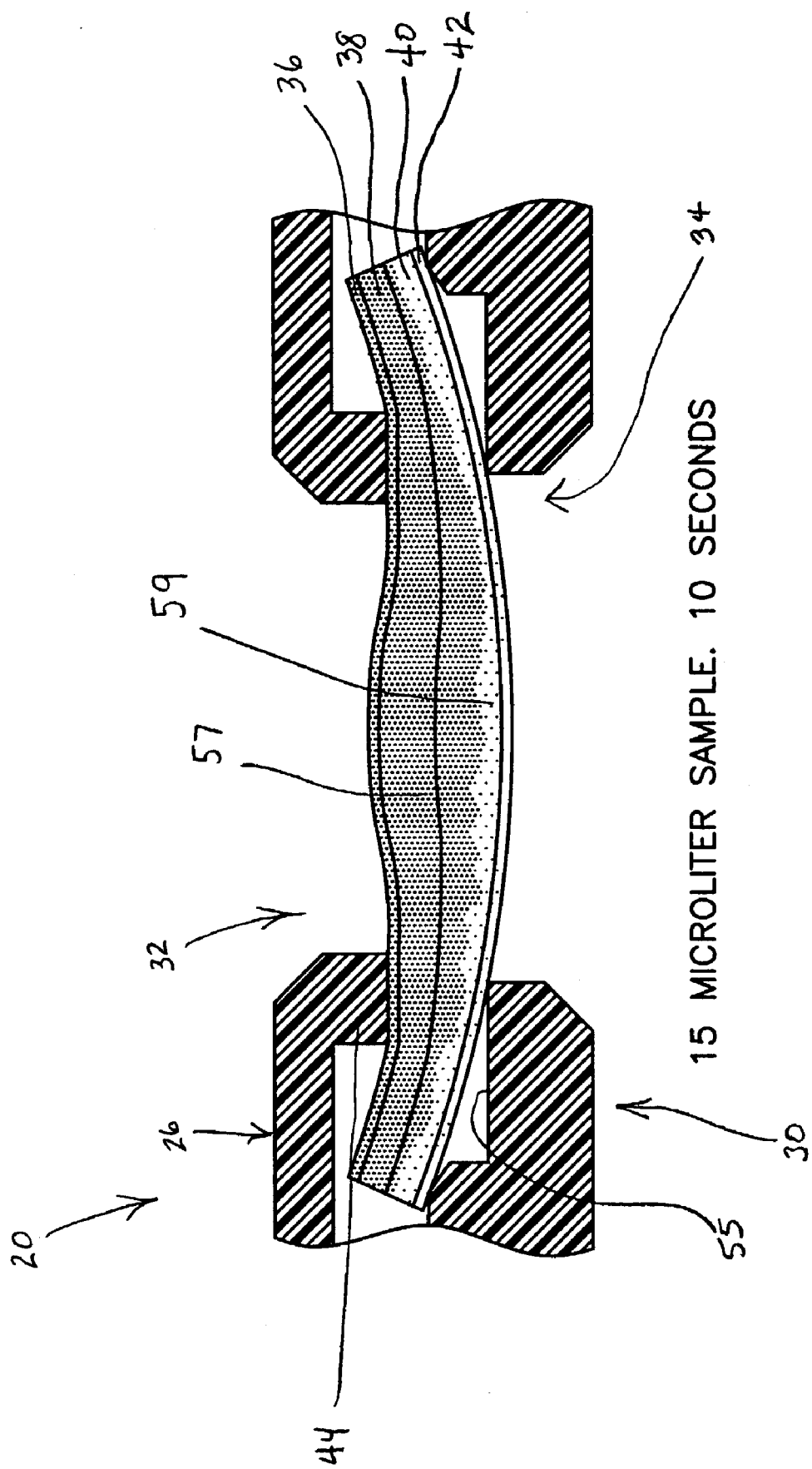
FIG. 23 is a cross sectional view of the test strip of FIG. 21 showing movement of blood and plasma at 10 seconds after the blood sample has been applied to the strip.
Figure 24:
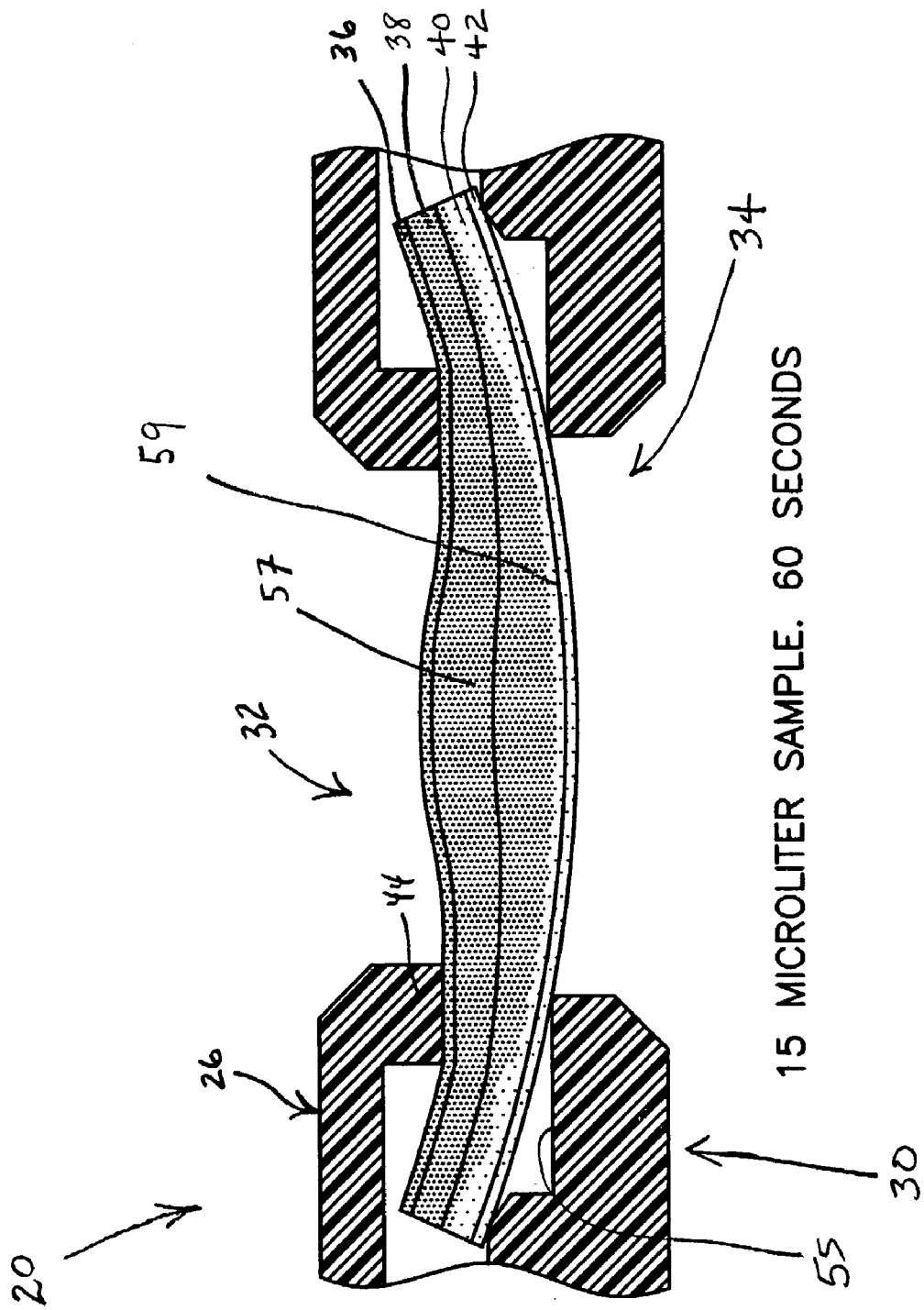
FIG. 24 is a cross sectional view of the test strip of FIG. 21 showing movement of blood and plasma at 60 seconds after the blood sample has been applied to the strip.

Turning now to FIG. 22, after 2 seconds, the test window area 32 is empty, fluid 57 having red blood cells has penetrated significantly into layer 40 and plasma 59 has almost certainly migrated into reaction layer 42. At 10 (ten) seconds (FIG. 23) fluid movement within strip 20 is substantially complete. At sixty (60) seconds (FIG. 24), the profiles of fluid 57 and plasma 59 have barely changed from those at ten (10) seconds (FIG. 23). Thus, the cryogenic micrography studies show that fluid movement in strip 20 drops off exponentially after only a few seconds. The reaction in layer 42 to produce color, however, takes much longer in comparison with fluid movement. It is estimated that substantially all of the plasma that will produce the color is present in layer 42 within ten–fifteen seconds, but the color producing reaction may take from sixty (60) to ninety (90) seconds to reach an endpoint.

Experiments were conducted to determine the relative percentage of red blood cells retained in layer 38 as compared to layer 40. Blood was applied to several test strips 20, and the strips were allowed to react. About ninety (90) seconds after the sample was deposited, the strips were disassembled and layers 38 and 40 were each immersed into separate test tubes containing an agent to cause red blood cell lysis. After three (3) minutes, layers 38 and 40 were removed from the solutions, and the solutions were scanned in a spectrophotometer between 500 and 600 nm to correlate the absorbance of the samples with their relative amount of hemoglobin. From these tests, it has been found that approximately 80% of red blood cells are retained in layer 38, with the remaining 20% being retained in layer 40. These percentages would be expected to be substantially the same even 10 seconds after blood application to the strip, since, as noted above, fluid movement is substantially complete by that time. Of course, the relative percentages just noted may vary from strip to strip and from sample to sample. Incidentally, it should be understood that the fluid containing red blood cells 57 contains more red blood cells in layer 38 then in layer 40. Fluid 57 is shown as a homogeneous shade in FIGS. 21–24 because of limitations in illustrations and because fluid 57 becomes saturated with red color with only a small percentage of red blood cells therein. Additional red cells do not make the color deeper. Thus, the depth of the red color of blood with 20% red blood cells remaining is not easily distinguishable from blood having 80% of red blood cells remaining, and FIGS. 21–24 reflect this.

Vertical Flow

Figure 3A:
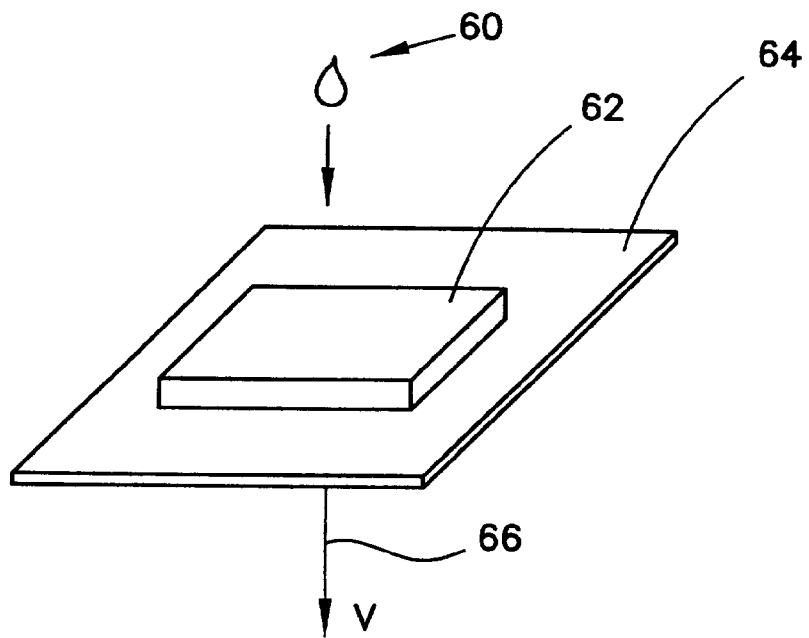
FIG. 3A is a perspective view of a test strip layer in accordance with the present invention, illustrating a plane defined by the layer.

While the "vertical flow" or absence of tangential flow has been explained above, the same is illustrated with reference to FIG. 3A. As shown, blood drop 60 is deposited onto layer 62. Layer 62 defines a plane 64 that is substantially parallel therewith. Transfer of fluid through layer 62 is normal or perpendicular to plane 64, or in the direction of vector V, shown at reference numeral 66. Thus, there is no substantial migration of fluid from one side of layer 62 to the other. Simply put, with the present invention, fluid flow is through layer 62, not across it.

While a preferred embodiment incorporating the principles of the present invention has been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of determining concentration of HDL cholesterol in a whole blood sample containing non-HDL cholesterol, said method comprising:
    a) providing a test strip holder and a test strip; said test strip holder including an application window and a rest reading window, said windows comprising vertically aligned openings in said holder; said test strip comprising a layered stack comprising a red blood cell separation layer, a non-HDL separation chemistry layer, and an HDL reaction layer; said non-HDL cholesterol separation chemistry layer containing non-HDL cholesterol separation chemicals for separating the non-HDL blood components from the HDL blood components so that the non-HDL components do not participate in the reaction in said HDL reaction layer; said HDL reaction layer containing chemicals for reacting with said HDL, said layers arranged in a vertical stack with said HDL reaction layer at the bottom of said stack; said test strip located in said test strip holder between said windows, with said reaction layer adjacent said test reading window;
    b) applying blood to the top of said stack through said application window and permitting fluid from said blood to flow vertically downward in said stack to said HDL reaction layer without substantial lateral migration of fluid below said red blood cell separation layer;
    c) separating said red blood cells from a fluid portion of said blood;
    d) separating said non-HDL cholesterol from said HDL cholesterol with said non-HDL cholesterol separation chemicals;
    e) reacting said HDL with said chemicals in said HDL reaction layer; and
    f) reading a property of said reaction layer through said reading window to determine said concentration of HDL cholesterol.

2. The method of claim 1 wherein:
    said providing comprises providing said red blood cell separation layer without including an agglutinin or a coagulant;
    and said separating said red blood cells is performed without agglutinizing or coagulating said red blood cells.

3. The method of claim 1 wherein said reacting comprises generating a color response and said method further comprises reading said colored response at a location that is substantially vertically aligned with the blood application area of said stack.

4. The method of claim 1 wherein said providing said red blood cell separation layer comprises providing glass fibers having a first average diameter and glass fibers having a second average diameter that is less than said first average diameter.

5. The method of claim 1 wherein said providing said red blood cell separation layer comprises impregnating said red blood cell separation layer with a salt.

6. The method of claim 5 wherein said impregnating comprises impregnating said red blood cell separation layer with a solution in which the salt concentration comprises about 0.5–3.0% by weight of said solution.

7. The method of claim 1 wherein said providing said red blood cell separation layer comprises impregnating said red blood cell separation layer with a wetting agent.

8. The method of claim 7 wherein said providing said red blood cell separation layer comprises impregnating said red blood cell separation layer with a sugar.

9. The method of claim 8 wherein said impregnating comprises impregnating said red blood cell separation layer with a sorbitol solution, the concentration of which comprises 3% to 10% sorbitol by weight of said solution.

10. The method of claim 1 wherein said providing said non-HDL cholesterol separation chemistry layer comprises impregnating said non-HDL cholesterol separation chemistry layer with a precipitant, and said separating said non-HDL cholesterol from said HDL cholesterol comprises precipitating said non-HDL cholesterol.

11. The method of claim 10 wherein said providing said non-HDL cholesterol separation chemistry layer comprises impregnating said non-HDL cholesterol separation chemistry layer with phosphotungstic acid (PTA).

12. The method of claim 11 wherein said providing said non-HDL cholesterol separation chemistry layer comprises impregnating said non-HDL cholesterol separation chemistry layer with said PTA and a divalent cation.

13. The method of claim 1 wherein said providing comprises stacking said red blood cell separation layer above said non-HDL cholesterol separation chemistry layer.

14. The method of claim 13 wherein said providing comprises providing a red blood cell separation layer comprising glass fiber.

15. The method of claim 14 wherein said providing said red blood cell separation layer comprises providing a first glass fiber layer with glass fibers having a first average diameter and providing a second glass fiber layer having glass fibers having a second average diameter that is less than said first average diameter.

16. The method of claim 15 wherein said providing said non-HDL cholesterol separation layer comprises providing said second glass fiber layer and impregnating said second glass fiber layer with said non-HDL cholesterol separation chemicals.

17. The method of claim 1 wherein:
said providing further comprises providing said layered stack with a dispersement layer above said red blood cell separation layer, said non-HDL separation chemistry layer, and said HDL detection layer; and
said method further comprising permitting said blood to disperse laterally across said dispersement layer.

18. A method as in claim 17 wherein said providing said dispersement layer comprises providing a woven mesh material.

19. A method of determining concentration of HDL cholesterol in a whole blood sample, said method comprising:
a) providing a layered stack comprising a dispersement layer, a red blood cell separation layer, a non-HDL separation chemistry layer, and an HDL reaction layer; said red blood cell separation layer not containing an agglutinin or a coagulant; said non-HDL cholesterol separation chemistry layer containing non-HDL cholesterol separation chemicals for separating the non-HDL blood components from the HDL blood components so that the non-HDL components do not participate in the reaction in said HDL reaction layer; said HDL reaction layer containing chemicals for reacting with said HDL; said layers arranged in a vertical stack with said dispersement layer at the top and said HDL reaction layer at the bottom;
b) applying blood to said dispersement layer and permitting fluid from said blood to first flow laterally across said dispersement layer and then to flow vertically downward in said stack to said HDL reaction layer without substantial lateral migration of fluid below said dispersement layer;
c) separating said red blood cells from a fluid portion of said blood in said red blood cell separation layer;
d) separating said non-HDL cholesterol from said HDL cholesterol using said non-HDL cholesterol separation chemicals;
e) reacting said HDL in said HDL reaction layer in a colorimetric reaction; and
f) determining the HDL cholesterol concentration in said reaction layer by measuring the reflectance of said reaction layer after said colorimetric reaction.

20. The method of claim 19 wherein said providing comprises stacking said red blood cell separation layer above said non-HDL cholesterol separation chemistry layer.

* * * * *